US010653592B2

(12) United States Patent
Baxter et al.

(10) Patent No.: US 10,653,592 B2
(45) Date of Patent: May 19, 2020

(54) MICROCAPSULES AND COMPOSITIONS PROVIDING CONTROLLED RELEASE OF ACTIVES

(71) Applicant: Noxell Corporation, Hunt Valley, MD (US)

(72) Inventors: Elaine Baxter, Egham (GB); Olivier Cayre, Leeds Yorkshire (GB); Simon Biggs, Brisbane Queensland (AU); Kirsty Scott Stark, Buckinghamshire (GB); Alison Louise Tasker, Toowong Western Australia (AU); James P Hitchcock, Leeds Yorkshire (GB)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 15/768,784

(22) PCT Filed: Oct. 26, 2016

(86) PCT No.: PCT/US2016/058899
§ 371 (c)(1),
(2) Date: Apr. 16, 2018

(87) PCT Pub. No.: WO2017/075074
PCT Pub. Date: May 4, 2017

(65) Prior Publication Data
US 2018/0289597 A1    Oct. 11, 2018

Related U.S. Application Data

(60) Provisional application No. 62/246,583, filed on Oct. 26, 2015, provisional application No. 62/246,586, (Continued)

(51) Int. Cl.
*A61K 8/11*   (2006.01)
*B01J 13/22*  (2006.01)
(Continued)

(52) U.S. Cl.
CPC ............... *A61K 8/11* (2013.01); *A61K 8/19* (2013.01); *A61K 8/22* (2013.01); *A61Q 5/08* (2013.01);
(Continued)

(58) Field of Classification Search
None
See application file for complete search history.

(56) References Cited

U.S. PATENT DOCUMENTS 3,788,955 A  *  1/1974  Crites et al. ............. B01J 13/02
                                                     205/145
4,576,737 A  *  3/1986  Johnson .................. A23F 3/405
                                                     101/424.1
(Continued)

FOREIGN PATENT DOCUMENTS

CN    108348885 A   7/2018
DE    2207211 A1   10/1972
(Continued)

OTHER PUBLICATIONS

"International Application Serial No. PCT/US2016/058899, International Preliminary Report on Patentability dated May 11, 2018", 13 pgs.
(Continued)

*Primary Examiner* — Robert A Wax
*Assistant Examiner* — Melissa S Mercier
(74) *Attorney, Agent, or Firm* — Schwegman Lundberg & Woessner, P.A.

(57) ABSTRACT

According to the present invention, there are provided microcapsules comprising an emulsion droplet encapsulated by a metallic film, wherein the emulsion droplet comprises an emulsifier disposed around a liquid core material. The present invention also provides processes for preparing the microcapsules, as well as formulations comprising the same.

(Continued)

The present invention further provides for certain consumer products comprising: an adjunct material; and a plurality of microcapsules, said microcapsules comprising: an emulsion droplet encapsulated by a metallic film, wherein the emulsion droplet comprises an emulsifier disposed around a liquid core material.

9 Claims, 6 Drawing Sheets

Related U.S. Application Data filed on Oct. 26, 2015, provisional application No. 62/246,593, filed on Oct. 26, 2015, provisional application No. 62/246,596, filed on Oct. 26, 2015.

(51) Int. Cl.

| | | |
|---|---|---|
| *A61K 8/19* | (2006.01) | |
| *C11D 3/50* | (2006.01) | |
| *C09B 67/02* | (2006.01) | |
| *B01J 13/02* | (2006.01) | |
| *A61Q 13/00* | (2006.01) | |
| *C11D 17/00* | (2006.01) | |
| *A61K 8/22* | (2006.01) | |
| *A61Q 5/08* | (2006.01) | |
| *A61Q 5/10* | (2006.01) | |
| *A61K 9/50* | (2006.01) | |

(52) U.S. Cl.
CPC .............. *A61Q 5/10* (2013.01); *A61Q 13/00* (2013.01); *B01J 13/02* (2013.01); *B01J 13/22* (2013.01); *C09B 67/0097* (2013.01); *C11D 3/505* (2013.01); *C11D 17/0039* (2013.01); *A61K 9/501* (2013.01); *A61K 2800/41* (2013.01); *A61K 2800/412* (2013.01); *A61K 2800/5922* (2013.01)

(56) References Cited

U.S. PATENT DOCUMENTS

| | | | | |
|---|---|---|---|---|
| 7,854,771 | B2 * | 12/2010 | Boutique | ............ C11D 3/3788 |
| | | | | 510/392 |
| 8,075,664 | B1 * | 12/2011 | Wang | ...................... B01J 13/02 |
| | | | | 75/252 |
| 2008/0272331 | A1 | 11/2008 | Mohapatra et al. | |

FOREIGN PATENT DOCUMENTS

| | | | |
|---|---|---|---|
| WO | WO-2009037482 A2 * | 3/2009 | .............. A61K 8/11 |
| WO | WO-2009037482 A2 | 3/2009 | |
| WO | WO-2017075074 A1 | 5/2017 | |

OTHER PUBLICATIONS

"Application Serial No. PCT/US2016/058899, Invitation to Pay Add'l Fees and Partial Search Rpt dated Dec. 13, 2016", 10 pgs.

"International Application Serial No. PCT/US2016/058899, International Search Report dated Feb. 6, 2017", 7 pgs.

"International Application Serial No. PCT/US2016/058899, Written Opinion dated Feb. 6, 2017", 11 pgs.

Cayre, Olivier J., "Polymer-based Functional Particulates: Design, Synthesisand Applications", [Online]. [retrieved on Feb. 11, 2016]. Retrieved from the Internet: http://www.uc.pt/fctucjdeqjecoflocjrepositoryjnews_files/CPEG_Research_Geneva_17-09-15 OLIVIER. pdf, (Nov. 11, 2014), 19-42.

James, P Hitchcock, et al., "Long-Term Retention of Small, Volatile Molecular Species within Metallic Microcapsules", ACS Applied Materials and Interfaces, voi. 7, No. 27,, (Jul. 15, 2015), 14808-14815.

"European Application Serial No. 16791505.7, Response filed Dec. 13, 2018 to Communication Pursuant to Rules 161(2) and 162 EPC dated Jun. 4, 2018", w English Claims, 14 pgs.

"Brazilian Application Serial No. BR112018 007321-0, Office Action dated Mar. 18, 2020", 5 pgs.

"European Application Serial No. 16791505.7, Communication Pursuant to Article 94(3) EPC dated Mar. 13, 2020", 4 pgs.

Olivier, J Cayre, "Polymer-based Functional Particulates: Design, Synthesis and Applications".

* cited by examiner

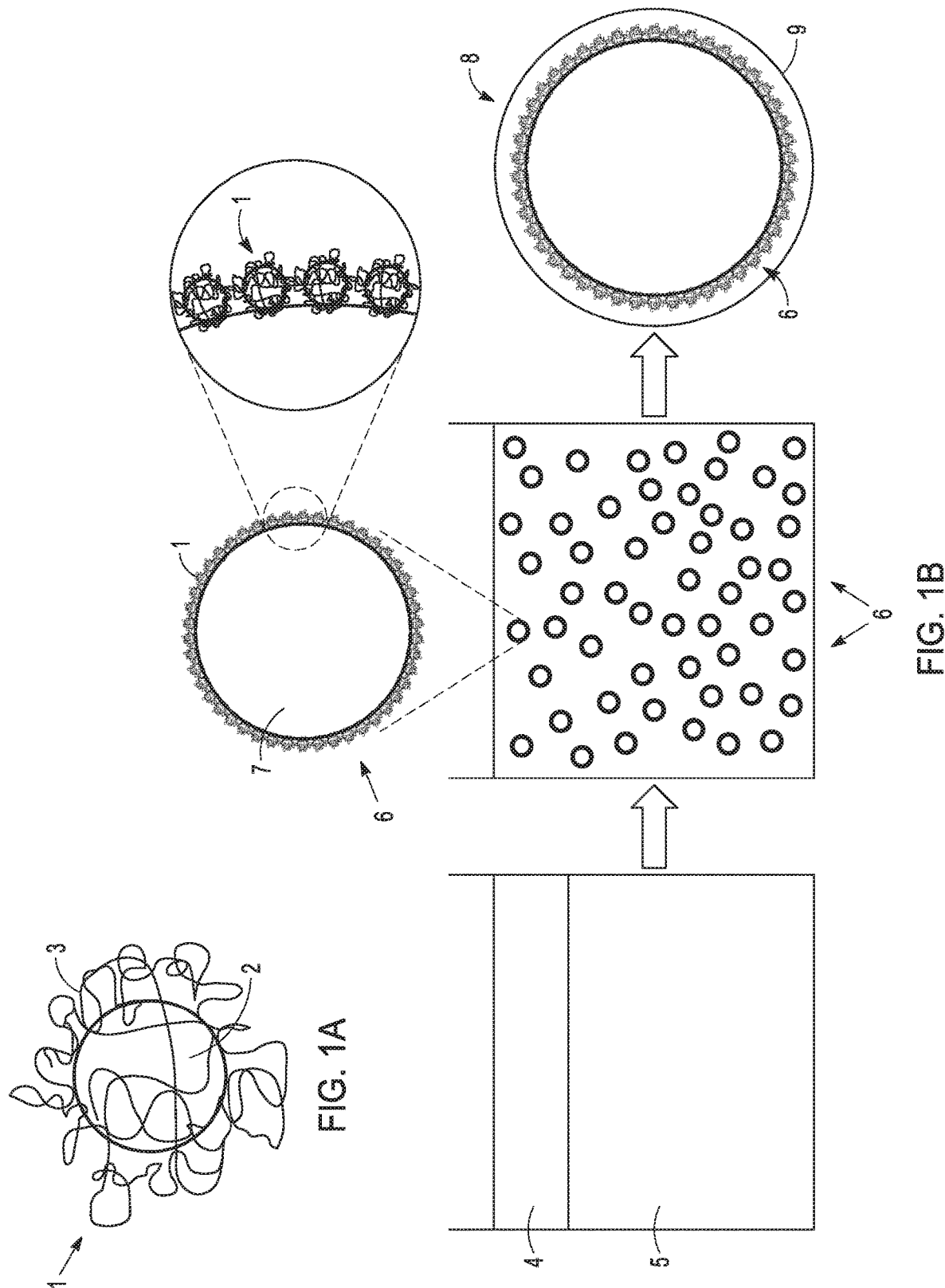

MICROCAPSULES AND COMPOSITIONS PROVIDING CONTROLLED RELEASE OF ACTIVES

CLAIM OF PRIORITY

This application is a U.S. National Stage Filing under 35 U.S.C. 371 from International Application No. PCT/US2016/058899, filed on 26 Oct. 2016, and published as WO 2017/075074 on 4 May 2017, which claims the benefit of priority to U.S. Provisional Application Ser. No. 62/246,583, filed on Oct. 26, 2015; 62/246,586, filed on Oct. 26, 2015; 62/246,593, filed on Oct. 26, 2015, and 62/246,596, filed on Oct. 26, 2015 which applications are incorporated herein by reference in their entirety.

FIELD OF THE INVENTION

The present disclosure generally relates to consumer products and methods of making a consumer product including microcapsules that contain a liquid core material. The present invention relates to microcapsules comprising a liquid core material, to processes for their preparation and to formulations comprising the same. More particularly, the present invention relates to microcapsules comprising a liquid core material which can be released in a controlled manner during use. The microcapsules find application in fine fragrance formulations and other consumer products where controlled release of active ingredients is desired.

BACKGROUND OF THE INVENTION

The encapsulation of liquid substances and their controlled, targeted delivery is important to industry. However, the efficient encapsulation of liquid substances, especially volatile substances, has proven difficult. Although applications of encapsulation techniques are increasing year on year, there remain significant shortcomings and limitations. In particular, the encapsulation of volatile compounds is an area in which little progress has been made.

Particular problems are encountered in the encapsulation of perfume oils, which are volatile substances found in fine fragrances and other fragrance formulations. Although the use of microcapsules to encapsulate perfume oils has been proposed, fragrance formulations typically contain polar solvents such as ethanol in which the microcapsules are dispersed. These polar solvents can readily penetrate the wall of the microcapsules, causing the perfume oils to leach prematurely from the microcapsules. It would be desirable to provide microcapsules which enable perfume oils to be released in a controlled manner during use, e.g. by rupturing the microcapsules during normal human movement.

Various processes for microencapsulation are known. Unfortunately, many microcapsules manufactured have drawbacks that include, but are not limited to: (1) they cannot be formulated in certain classes of products due to strict formulation limits, (2) they are highly permeable when incorporated into certain products such as those that contain high levels of surfactant and solvents, resulting in the premature release of the active. (3) they can only effectively encapsulate a limited breadth of actives, and (4) they either are so stable that they do not release the active in use or have insufficient mechanical stability to withstand the processes required to incorporate them in and/or make a consumer product and (5) they do not adequately deposit on the situs that is being treated with consumer product that contains the microcapsules. Thus, there exists a need for microcapsules that can improve on at least one of these drawbacks.

There is a further need in the art for improved microcapsules for encapsulating liquid substances, especially microcapsules which exhibit an improved release profile. In particular, there is a need for microcapsules for encapsulating liquid substances such as perfume oils, wherein the microcapsules are substantially impermeable to polar solvents such as ethanol yet, at the same time, are capable of releasing their contents in a controlled manner during use. There is also a need for improved processes for the preparation of microcapsules.

SUMMARY OF THE INVENTION

According to a first aspect of the present invention, there is provided a microcapsule comprising an emulsion droplet encapsulated by a metallic film, wherein the emulsion droplet comprises an emulsifier disposed around a liquid core material.

According to a second aspect of the present invention, there is provided a microcapsule comprising an emulsion droplet encapsulated by a metallic film, wherein:
the emulsion droplet comprises an emulsifier disposed around a liquid core material; and
the metallic film is formed on said emulsion droplet.

According to a third aspect of the present invention, there is provided a process for preparing a microcapsule of the invention, the process comprising:
providing an emulsion droplet comprising an emulsifier disposed around a liquid core material; and
forming a metallic film on the emulsion droplet such that the emulsion droplet is encapsulated by the metallic film.

According to a fourth aspect of the present invention, there is provided a microcapsule comprising an emulsion droplet encapsulated by a metallic film, wherein:
the emulsion droplet comprises an emulsifier disposed around a liquid core material; and
wherein the emulsifier comprises nanoparticles of a first metal, and wherein the metallic film comprises a layer of a second metal.

According to a fifth aspect of the present invention, there is provided a microcapsule comprising an emulsion droplet encapsulated by a metallic film, wherein:
the emulsion droplet comprises an emulsifier disposed around a liquid core material; and
the metallic film is formed on said emulsion droplet;
wherein the emulsifier comprises nanoparticles of a first metal and a stabilizer which stabilizes the nanoparticles, and wherein the metallic film comprises a layer of a second metal formed on said emulsifier.

According to a sixth aspect of the present invention, there is provided a process for preparing a microcapsule of the invention, the process comprising:
providing an emulsion droplet comprising an emulsifier disposed around a liquid core material; and
forming a metallic film on the emulsion droplet such that the emulsion droplet is encapsulated by the metallic film;
wherein the emulsifier comprises nanoparticles of a first metal and a stabilizer which stabilizes the nanoparticles, and wherein the step of forming the metallic film comprises forming a layer of a second metal on said emulsifier.

According to a seventh aspect of the present invention, there is provided a microcapsule comprising an emulsion droplet encapsulated by a metallic film, wherein the emulsion droplet comprises an emulsifier disposed around a liquid core material, wherein the emulsion droplet comprises nanoparticles of a first metal, and wherein the metallic film comprises a layer of a second metal.

According to an eighth aspect of the present invention, there is provided a microcapsule comprising an emulsion droplet encapsulated by a metallic film, wherein:
  the emulsion droplet comprises an emulsifier disposed around a liquid core material; and
  the metallic film is formed on said emulsion droplet;
  wherein the emulsion droplet comprises nanoparticles of a first metal adsorbed on said emulsifier and wherein the metallic film comprises a layer of a second metal formed on the emulsifier and adsorbed nanoparticles.

According to a ninth aspect of the present invention, there is provided a process for preparing a microcapsule of the invention, the process comprising:
  providing an emulsion droplet comprising an emulsifier disposed around a liquid core material;
  adsorbing nanoparticles of a first metal on said emulsifier; and
  forming a metallic film on the emulsion droplet such that the emulsion droplet is encapsulated by the metallic film;
  wherein the step of forming the metallic film comprises forming a layer of a second metal on the emulsifier and adsorbed nanoparticles.

According to a tenth aspect of the present invention, there is provided a consumer product comprising a composition, said composition comprising:
an adjunct material; and
a plurality of microcapsules, said microcapsules comprising:
  an emulsion droplet encapsulated by a metallic film, wherein the emulsion droplet comprises an emulsifier disposed around a liquid core material.

According to an eleventh aspect of the present invention, there is provided there is provided a consumer product comprising a composition, said composition comprising:
an adjunct material; and
a plurality of microcapsules, said microcapsules comprising:
  an emulsion droplet encapsulated by a metallic film, wherein:
    the emulsion droplet comprises an emulsifier disposed around a liquid core material; and
    the metallic film is formed on said emulsion droplet.

According to a twelfth aspect of the present invention, there is provided a method of making a composition, said method comprising the steps:
combining an adjunct material with a plurality of coated microcapsules to form a composition;
  wherein said coated microcapsules comprise:
an emulsion droplet encapsulated by a metallic film, wherein the emulsion droplet comprises an emulsifier disposed around a liquid core material;
  wherein said composition is a component of a consumer product.

In other aspects, the present invention provides a plurality of microcapsules of the invention, as well as formulations comprising the same. Also provided are methods of fragrancing a substrate using a microcapsule of the present invention.

The microcapsules offer various advantages and benefits. In particular, volatile liquid substances such as perfume oils can be encapsulated in microcapsules which are substantially impermeable to polar solvents such as ethanol yet, at the same time, can be ruptured during use. Moreover, the preparation processes disclosed herein enable the microcapsules to be prepared in a facile manner. In particular, the processes described herein may enable a metallic film to be applied in only a small number of steps.

BRIEF DESCRIPTION OF THE DRAWINGS

FIG. 1 is a schematic diagram illustrating an exemplary process for preparing microcapsules of the present invention. Depicted in FIG. 1a is an emulsifier 1 comprising nanoparticle 2 of a first metal which is sterically stabilized by a polymeric stabilizer 3. FIG. 1b depicts a process for preparing a microcapsule in which the emulsifier shown in FIG. 1a is used. In the first step of the illustrated process, non-aqueous phase 4 and aqueous phase 5 containing emulsifier 1 are emulsified to give emulsion droplets 6, each comprising emulsifier 1 disposed around a liquid core 7 of the non-aqueous phase. In the second step of the process, a layer of a second metal is formed on the emulsion droplets 6, yielding microcapsules 8 comprising an emulsion droplet 6 encapsulated by a metallic film 9.

FIGS. 3 to 6 provide optical micrographs, cryoTEM and SEM images obtained at various stages of preparation of a microcapsule of the invention, the microcapsule comprising a Pt-PVP emulsifier, a hexadecane core and a gold film. Specifically, FIG. 4 is a cryoTEM image of the emulsion droplets. FIG. 5 is a reflected light optical micrograph showing the microcapsules having a continuous gold film on their surface.

DETAILED DESCRIPTION OF THE INVENTION

Figure 2A:
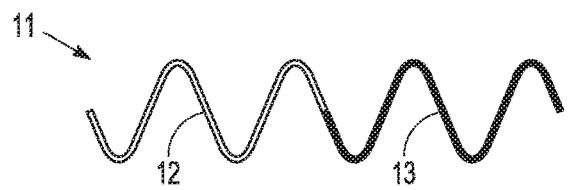
FIG. 2 is a schematic diagram illustrating an alternative process for preparing microcapsules of the present invention. Depicted in FIG. 2a is an emulsifier 11 which may be a diblock copolymer comprising a hydrophobic block 12 and a hydrophilic block 13.
FIG. 2b depicts a process in which the emulsifier shown in FIG. 2a is used. In the first step of the illustrated process, non-aqueous phase 14 and aqueous phase 15 containing emulsifier 11 are emulsified to give emulsion droplets 16, each comprising emulsifier 11 disposed around a liquid core 17 of the non-aqueous phase. In the second step of the process, particles of a first metal 18 are adsorbed onto the surface of the emulsion droplets 16, on the hydrophilic block of emulsifier 11. In the third step, a layer of a second metal is formed on the emulsion droplets, yielding microcapsules 19 comprising an emulsion droplet 16 encapsulated by a metallic film 20.
Figure 2B:
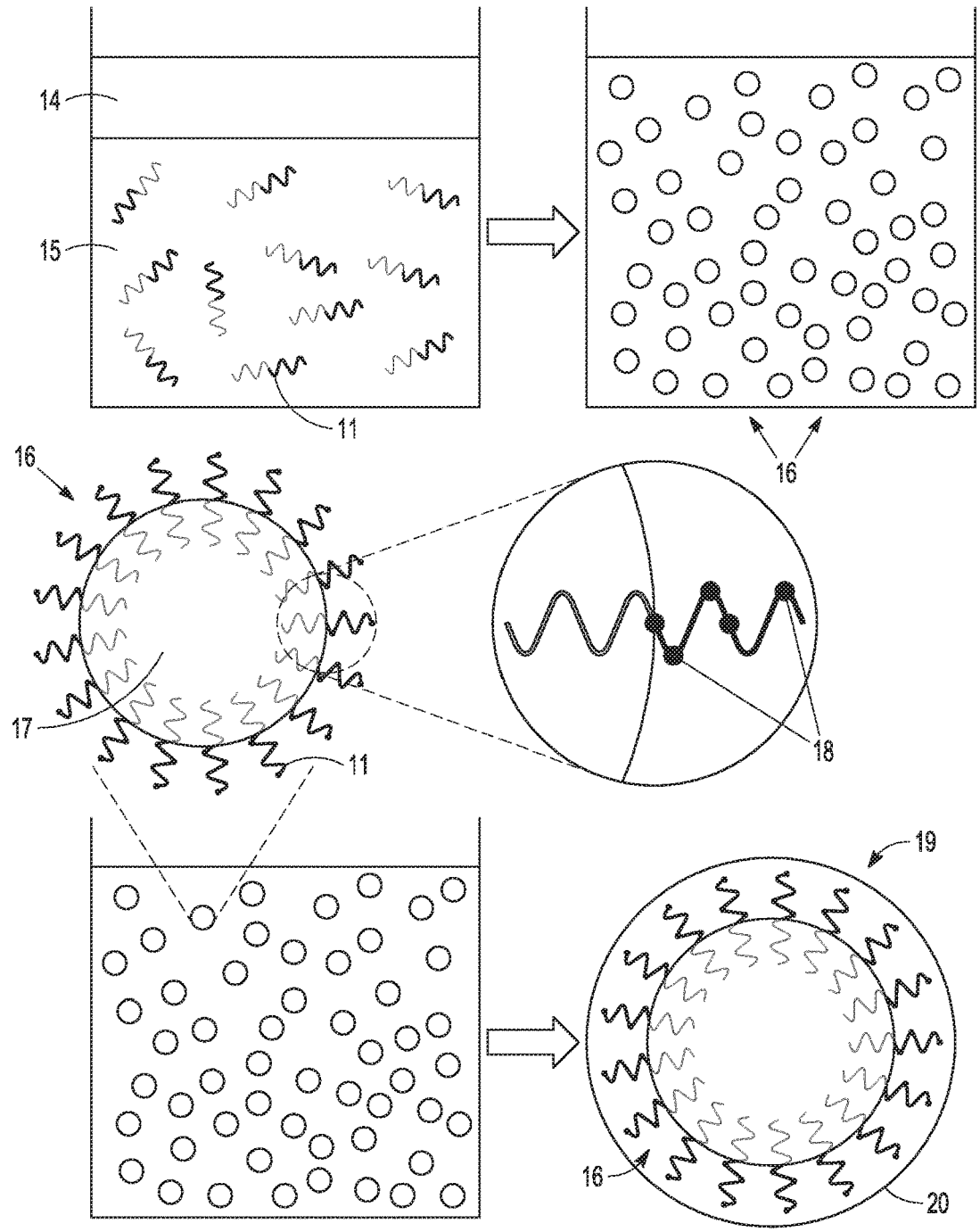

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Adjunct material" is any material that is not a microcapsule and that is added to the microcapsules to form the consumer product. The adjunct material may take many forms, and it is to be appreciated that an adjunct material may be a pure substance or include more than one type of material such that the adjunct material is collection/mixture of different materials, arranged in any manner. Adjunct materials, however, are limited to those used in consumer products.

"Free of" means that the stated ingredient has not been added to the composition. However, the stated ingredient may incidentally form as a byproduct or a reaction product of the other components of the composition.

"Nonvolatile" refers to those materials that liquid or solid under ambient conditions and have a measurable vapor pressure at 25° C. These materials typically have a vapor pressure of less than about 0.0000001 mmHg, and an average boiling point typically greater than about 250° C.

"Soluble" means at least about 0.1 g of solute dissolves in 100 ml of solvent at 25° C. and 1 atm of pressure.

"Substantially free of" means an amount of a material that is less than 1%, 0.5%, 0.25%, 0.1%, 0.05%, 0.01%, or 0.001% by weight of a composition.

"Derivatives" as used herein, include but are not limited to, amide, ether, ester, amino, carboxyl, acetyl, and/or alcohol derivatives of a given chemical.

"Skin care actives" as used herein, means substances that when applied to the skin, provide a benefit or improvement to the skin. It is to be understood that skin care actives are useful not only for application to skin, but also to hair, nails and other mammalian keratinous tissue.

"Situs" means the location where the composition is applied. Non-limiting examples of a situs include mammalian keratinous tissue and clothing.

"Volatile," as used herein, unless otherwise specified, refers to those materials that are liquid or solid under ambient conditions and which have a measurable vapor pressure at 25° C. These materials typically have a vapor pressure of greater than about 0.0000001 mmHg, alternatively from about 0.02 mmHg to about 20 mmHg, and an average boiling point typically less than about 250° C., alternatively less than about 235° C.

When the stability of microcapsule is compromised by inclusion in a composition, a potential solution is to separate the microcapsule from the composition by using a container with separate reservoirs for storing the incompatible ingredients. However, separating the microcapsules from the composition is not always a viable option. Accordingly, the microcapsules disclosed can be made to better control permeability characteristics of actives. In this regard, the microcapsules disclosed herein are surprisingly better able to contain liquid contents without leakage over time.

Liquid Core Material

The microcapsules of the present invention comprise an encapsulated emulsion droplet, wherein the emulsion droplet comprising an emulsifier disposed around a liquid core material. The term "liquid core material" as used herein refers to a core material formed of one or more components, at least 90% by weight of which are liquid at standard ambient temperature and pressure. The term "standard ambient temperature and pressure" (or "STP") refers to a temperature of 25° C. and an absolute pressure of 100 kPa. Preferably, the liquid core material comprises at least 95% by weight, e.g. at least 98% by weight, of one or more components which are liquid at standard ambient temperature and pressure. In an embodiment, the liquid core material consists of one or more components which are liquid at standard ambient temperature and pressure.

The liquid core material may be present in the microcapsule in an amount of at least 1% by weight of the microcapsule, preferably in an amount of at least 30% by weight, and more preferably in an amount of at least 60% by weight. In a preferred embodiment, the liquid core material is present in the microcapsule in an amount of from 40 to 98% by weight of the microcapsule, preferably from 50 to 98% by weight, more preferably from 60 to 98% by weight.

In an embodiment, the liquid core material comprises one or more components which are volatile. Unless otherwise specified, the term "volatile" as used herein refers to those materials that are liquid or solid under ambient conditions and which have a measurable vapour pressure at 25° C. These materials typically have a vapour pressure of greater than about 0.0000001 mm Hg, e.g. from about 0.02 mm Hg to about 20 mm Hg, and an average boiling point typically less than about 250° C., e.g. less than about 235° C.

The liquid core material may consist of a single material or it may be formed of a mixture of different materials. In one embodiment, the liquid core material comprises one or more active ingredients (non-limiting examples of active ingredients include, but are not limited to, perfume oils, dyes, cooling sensates, warming sensates, pigments, and mixtures thereof). The microcapsules of the present invention described herein are useful with a wide variety of active ingredients (i.e., "core materials") including, by way of illustration and without limitation, perfumes; brighteners; insect repellants; silicones; waxes; flavors; vitamins; fabric softening agents; depilatories; skin care agents; enzymes; probiotics; dye polymer conjugate; dye clay conjugate; perfume delivery system; sensates in one aspect a cooling agent; attractants, in one aspect a pheromone; anti-bacterial agents; dyes; pigments; bleaches; flavorants; sweeteners; waxes; pharmaceuticals; fertilizers; herbicides and mixtures thereof. The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. Particularly useful encapsulated materials are volatile fragrances.

The liquid core material preferably comprises one or more components which are oil-soluble. The use of a liquid core material which is oil-soluble will be preferable having regard to, inter alia, the production of the emulsion droplets, which will typically be prepared by a process which involves the use of an oil-in-water emulsion in which the liquid core material is present in the non-aqueous (oil) phase. In an embodiment, the liquid core material is substantially free of water. In particular, the amount of water present in the liquid core material may be less than 5% by weight, e.g. less than 1% by weight, of the liquid core material. More preferably, the liquid core material consists of one or more oil-soluble components. Preferably, the liquid core material is substantially free of any polymerizable compounds. In particular, the amount of polymerizable compounds in the liquid core material is less than 5% by weight, e.g. less than 1% by weight, of the liquid core material. More preferably, the liquid core material is free of any polymerizable compounds.

In a particularly preferred embodiment, the liquid core material comprises a perfume oil formed of one or more perfume raw materials. The term "perfume oil" as used herein refers to the perfume raw material, or mixture of perfume raw materials, that is used to impart an overall pleasant odour profile to the liquid core material. Thus, where different perfume raw materials are present in the liquid core material, this term refers to the overall mixture of perfume raw materials in the liquid core material. The choice of the perfume raw materials defines both the odour intensity and character of the liquid core material. The perfume oils utilized in the microcapsules may be relatively simple in their chemical make-up, for example consisting of only a single perfume raw material, or they may comprise complex mixtures of perfume raw materials, all chosen to provide a desired odour.

The perfume oil may comprise one or more perfume raw materials having a boiling point of less than 500° C., e.g. less than 400° C., e.g. less than 350° C. The boiling points of many perfume raw materials are given in textbooks known in the art.

The one or more perfume raw materials will typically be hydrophobic. The hydrophobicity of a given compound may be defined in terms of its partition coefficient. The term "partition coefficient" as used herein refers to the ratio between the equilibrium concentration of that substance in n-octanol and in water, and is a measure of the differential solubility of said substance between these two solvents.

The term "log P" refers to the logarithm to the base 10 of the partition coefficient. Values of log P values can be readily calculated using a program called "C LOG P" which is available from Daylight Chemical Information Systems Inc., 30 Irvine Calif., USA or using Advanced Chemistry Development (ACD/Labs) Software 9 V 11.02 (© 1994-2014 ACD/Labs).

In an embodiment, the perfume oil comprises one or more perfume raw materials having a calculated log P (C log P) value of about −0.5 or greater, e.g. greater than 0.1, e.g. greater than 0.5, e.g. greater than 1.0. In an embodiment, the perfume oil consists of one or more perfume raw materials having a C log P value of greater than 0.1, e.g. greater than 0.5. e.g. greater than 1.0.

In an embodiment, the perfume oil comprises one or more perfume raw materials selected from aldehydes, esters, alcohols, ketones, ethers, alkenes, nitriles, Schiff bases, and mixtures thereof.

In an embodiment, the liquid core material comprises one or more perfume oils of natural origin. One or more of these perfume oils may be used with one or more of the perfume raw materials recited above.

The perfume oil may be present in the liquid core material in an amount of from 0.1 to 100% by weight of the liquid core material. In an embodiment, the liquid core material consists essentially, e.g. consists of, a perfume oil. In an embodiment, the perfume oil is present in the liquid core material in an amount of at least 10% by weight of the liquid core material, preferably at least 20% by weight, and more preferably at least 30% by weight. In an embodiment, the perfume oil is present in the liquid core material in an amount of 100% by weight, preferably less than 90% by weight, and preferably less than 80% by weight. Preferred liquid core materials contain from 10 to 100% by weight of a perfume oil, preferably from 20 to 100%, more preferably from 30 to 80%. In a preferred embodiment, the liquid core material consists essentially, more preferably consists of, a perfume oil.

The liquid core material may comprise one or more components in addition to the perfume oil. For example, the liquid core material may comprise one or more other hydrophobic ingredients, e.g. selected from skin care ingredients.

Emulsifier

The emulsion droplet comprises an emulsifier disposed around the liquid core material. Emulsion droplets may be formed by providing an oil-in-water emulsion in which droplets of an oil (non-aqueous) phase comprising the liquid core material are dispersed in a continuous aqueous phase, in the presence of an emulsifier. Emulsifiers (also known as stabilizers) stabilize the emulsion and reduce the likelihood of aggregation of the emulsion droplets. Emulsifiers normally stabilize the emulsion by orienting themselves at the oil phase/aqueous phase interface, thus establishing a steric and/or charged boundary layer around each droplet. This layer serves as a barrier to other particles or droplets preventing their intimate contact and coalescence, thereby maintaining a uniform droplet size.

The emulsifier may be a non-ionic, cationic, anionic, zwitterionic or amphoteric emulsifier. The emulsifier may be a polymer, a surfactant, a protein or a particle.

In a preferred embodiment, the emulsifier comprises a polymer. Preferably, the polymer comprises one or more groups selected from carboxyl, hydroxyl, amine, and ester groups. The polymer may be a homopolymer or a copolymer (e.g. a graft copolymer or a block copolymer). Examples of suitable polymers include poly(ethylene oxide), polyethylene glycol, poly(acrylic acid), poly(acrylamide), poly(ethylene imine) and poly(vinyl alcohol).

Preferably the polymer has a weight average molecular weight of at least 1 kDa, more preferably at least 10 kDa, more preferably at least 20 kDa. Preferably, the molecular weight of the polymer is from 1 to 100 kDa, more preferably from 10 to 80 kDa, more preferably from 30 to 60 kDa.

In an embodiment, the polymer is a non-ionic polymer. Examples of non-ionic polymers include, without limitation, poly(vinyl alcohol), poly(vinyl propylene), poly(ethylene glycol) and poly(vinyl pyrrolidone). Poly(vinyl pyrrolidone) is particularly preferred as a steric stabilizer.

In an embodiment, the polymer is a cationic polymer. Examples of cationic polymers include, without limitation, poly(allyl amine) polymers. e.g. poly(allyl amine hydrochloride).

In an embodiment, the polymer is an anionic polymer. Examples of anionic polymers include, without limitation, polyacids, e.g. poly(acrylic acid) or poly(methacrylic acid).

In an embodiment, the polymer is selected from poly (vinyl alcohol) (PVA), poly(vinyl pyrrolidone) (PVP), poly (acrylic acid) (PAA), poly(methacrylic acid) (PMA) and poly(ethylene glycol). More preferably, the polymer is poly (vinyl pyrrolidone) (PVP).

In an embodiment, the polymer is selected from polyoxyalkylene glycol alkyl ethers (e.g. polyoxyethylene glycol alkyl ethers and polyoxypropylene glycol alkyl ethers), sorbitan esters (e.g. polysorbates) and poly(isobutenyl) succinic anhydride amine derivatives.

In a particularly preferred embodiment, the polymer is poly(vinyl pyrrolidone) (PVP) or a di-block copolymer formed of a first block comprising a poly(aminoalkyl acrylate) and a second block comprising a poly(alkyl acrylate).

In other embodiments, the emulsifier is a surfactant. Examples of suitable surfactants include, without limitation, cetyl trimethylammonium bromide (CTAB), dodecyldimethyl ammonium bromide (DDAB) and sodium dodecyl sulfate (SDS).

The emulsion droplet may be formed by emulsifying the liquid core material into droplets in the presence of the emulsifier. In particular, the emulsion droplet may be prepared by: (i) providing a non-aqueous phase comprising the liquid core material; (ii) providing an aqueous phase; (iii) providing an emulsifier; and (iv) emulsifying the non-aqueous phase and the aqueous phase to form an emulsion comprising droplets of the non-aqueous phase dispersed within the aqueous phase, the droplets comprising the emulsifier disposed around the liquid core material.

The emulsifier may be provided in at least one of the aqueous and non-aqueous phases. Preferably, the emulsifier is provided as part of the aqueous phase. In an embodiment, the emulsifier is present in an amount of from 0.0001 to 50% by weight of the aqueous phase, preferably from 0.05 to 30%, and more preferably from 0.01 to 10% by weight.

The aqueous phase and the non-aqueous phase may be mixed in a ratio of from 500:1 to 1:2, preferably from 400:1 to 1:1, and more preferably from 250:1 to 2:1 by volume.

In each of the emulsification processes described herein, emulsification can be conducted using any suitable mixing device known in the art. For example, a homogenizer, colloid mill, ultrasonic dispersion device, ultrasonic emulsifier, microfluidic technique, or membrane emulsification technology may be used. In one embodiment, homogenizer or an ultrasonic emulsifier may be used.

The size of the emulsion droplets can be controlled by altering factors such as the stirring speed and the shape of the stirring blade or rotor blade of the stirrer or homomixer used during the emulsification step of the microencapsulation. In particular, the size of the emulsion droplets may be controlled by regulating the stirring speed, which in turn regulates the size of the droplets of the liquid core material in the emulsion. Other methods for controlling the size of the emulsion droplets include modifying the ratio of the aqueous phase to the non-aqueous phase and modifying the concentration of the emulsifier.

In the resulting emulsion droplet, the emulsifier is disposed around a droplet of the liquid core material. As illustrated in the Figures herein, the emulsifier molecules are distributed over the surface of the liquid core material and present a scaffold upon which the metallic film is formed. In embodiments, the emulsifier molecules are arranged on the surface of the liquid core material in a substantially uniform distribution.

As explained in more detail below, in some embodiments the emulsion droplet is formed using an emulsifier which comprises particles of a first metal. In other embodiments, particles of a first metal are adsorbed onto the emulsifier of the emulsion droplet. Preferred emulsifiers for use in these embodiments are discussed in more detail below.

In an embodiment, the emulsifier is cross-linked prior to formation of the metallic film. Cross-linking of the emulsifier may be advantageous in terms of stabilizing and strengthening the emulsion droplet. The cross-linking reaction will preferably take place in the non-aqueous phase. Preferred cross-linkers for use in the cross-linking reaction include molecules that are soluble in the non-aqueous phase and which comprise at least two reactive moieties, e.g. glutaraldehyde, diamines, polymeric diisocyanates such as tolylene 2,4-diisocyanate terminated poly(propylene glycols), and epoxy-containing molecules such as glycidyl methacrylate and poly(ethylene glycol) diglycidyl ethers. Other commercially available cross-linkers may also be used.

The emulsion droplet may have an average diameter of from 0.1 to 100 microns. Preferably, the emulsion droplet has an average diameter of from 1 to 30 microns and more preferably 10 to 20 microns. The emulsion droplet may be characterized using the procedure described in the Test Methods section herein.

Metallic Film

The microcapsules of the present invention further comprise a metallic film which encapsulates the emulsion droplet. The metallic film is formed directly on the emulsion droplet, rather than on a separate shell which encapsulates the emulsion droplet. The metallic film is preferably a continuous film which surrounds the surface of the emulsion droplet.

The emulsifier that is disposed around the liquid core material serves as a scaffold upon which the metallic film is formed. In a preferred embodiment, the emulsion droplet comprises particles of a first metal and the metallic film comprises a layer of a second metal formed on the particles of the first metal.

The particles of the first metal may be metal ions, nanoparticles, or larger particles. The particles are preferably nanoparticles. The term "nanoparticles" as used herein refers to particles having a particle size of from 1 to 200 nm. Preferably, the metal nanoparticles have a particle size of less than 100 nm, e.g. less than 50 nm. More preferably, the metal nanoparticles have a particle size of less than 10 nm, more preferably less than 5 nm, and more preferably less than 3 nm. In this regard, the use of smaller metal nanoparticles may result in the formation of a thinner metallic film. The nanoparticles will typically have a spheroidal geometry, but they may exist in more complex forms such as rods, stars, ellipsoids, cubes or sheets.

In an embodiment, the nanoparticles comprise gold, silver, copper, tin, cobalt, tungsten, platinum, palladium, nickel, iron or aluminium nanoparticles, or mixtures thereof. In an embodiment, the nanoparticles comprise an alloy of two or more metals, e.g. an alloy of two or more metals selected from gold, silver, copper, tin, cobalt, tungsten, platinum, palladium, nickel, iron and aluminium. In an embodiment, the nanoparticles comprise a metal oxide, e.g. aluminium oxide or an iron oxide. In an embodiment, the nanoparticles comprise core-shell particles comprising a core of a first metal or metal oxide surrounded by a shell of a second metal or metal oxide. In an embodiment, the nanoparticles consist of a single metal.

As described in more detail below, the layer of the second metal is preferably applied by an electroless plating procedure which is catalyzed by the particles of the first metal. It is therefore preferred that the particles of the first metal comprise a metal which catalyzes the electroless plating process.

The first metal may be selected from the transition metals and p-block metals, e.g. a metal selected from those metals listed in Groups 9 to 14 of the Periodic Table, in particular a metal selected from Groups 10, 11 and 14. Preferably, the first metal is a metal selected from nickel, palladium, platinum, silver, gold, tin and combinations thereof. Preferably, the first metal comprises platinum, silver, gold, or a mixture thereof.

The first and second metals may be the same or different. Preferably, the second metal is different to the first metal.

The second metal is preferably a metal that is capable of being deposited via an electroless plating process. The second metal may be a transition metal, e.g. a metal selected from those metals listed in Groups 9 to 14 of the Periodic Table, in particular a metal selected from Groups 10 and 11. Preferably, the second metal is a metal selected from silver, gold, copper and combinations thereof.

In an embodiment, the first metal is selected from Au, Pt, Pd, Sn, Ag and combinations thereof; and the second metal is selected from Au, Ag, Cu, Ni and combinations thereof.

In an embodiment, the first metal is selected from Au, Pt, Pd, Sn, Ag and combinations thereof (e.g. Sn/Ag) and the second metal is Au. In another embodiment, the first metal is selected from Sn, Pt, Ag, Au and combinations thereof (e.g. Pt/Sn) and the second metal is Ag. In another embodiment, the first metal is selected from Sn, Ag, Ni and combinations thereof (e.g. Sn/Ni or Sn/Ag) and the second metal is Cu. In another embodiment, the first metal is selected from Sn, Pd, Ag and combinations thereof (e.g. Sn/Pd) and the second metal is Ni.

In preferred embodiments, the first metal is Pt and the second metal is Au, the first metal is Au and the second metal is Ag; or the first metal is Au and the second metal is Cu. More preferably, the first metal is Au and the second metal is Ag; or the first metal is Pt and the second metal is Au.

The particles of the first metal are preferably present on the emulsion droplet in the form of a discontinuous layer such that, prior to application of the second metal, the surface of the emulsion droplet comprises regions comprising metal particles and regions in which metal particles are absent. The metal particles may be distributed over the surface of the emulsion droplet in a substantially uniform manner.

The thickness of the layer of the second metal may vary with the density of the particles of the first metal on the emulsion droplet, with a higher density of particles of the first metal typically encouraging the growth of a thinner film. In an embodiment, the particles are present on the surface of the emulsion droplet at a density of from 0.0001 to 0.1 $g/m^2$ of the surface area of the emulsion droplet, e.g. from 0.0005 to 0.05 $g/m^2$ of the surface area of the emulsion droplet, e.g. from 0.001 to 0.03 $g/m^2$ of the surface area of the emulsion droplet. The density of the particles on the emulsion droplet may be determined using the procedure described in the Test Methods section herein.

The particles of the first metal may be introduced in various ways. In an embodiment, the emulsion droplet is formed using an emulsifier which comprises nanoparticles of the first metal and a stabilizer which stabilizes the nanoparticles. In another embodiment, the emulsion droplet is formed and then contacted with nanoparticles of the first metal such that said particles are adsorbed on the emulsifier of the emulsion droplet. These methods are described in more detail below.

Deposition of the First Metal: Use of an Emulsifier Comprising Metal Particles

In an embodiment, the particles of the first metal are introduced by forming the emulsion droplet using an emulsifier which comprises particles of the first metal.

In an embodiment, the emulsion droplet is formed using an emulsifier which comprises nanoparticles of the first metal and a stabiliser which stabilises the nanoparticles.

In one embodiment, the nanoparticles of the first metal are sterically-stabilized nanoparticles. Sterically-stabilized nanoparticles are known in the art and generally comprise a polymer or other macromolecule which is adsorbed on the surface of the metal particles, forming a protective sheath around the particles and minimising aggregation.

In one embodiment, the emulsifier comprises nanoparticles of the first metal and polymeric stabilizer, wherein the nanoparticles are sterically-stabilized by the polymeric stabilizer. Preferably, the polymeric stabilizer is a polymer which comprises one or more groups selected from carboxyl, hydroxyl, amine, and ester groups. The polymer may be a homopolymer or a copolymer (e.g. a graft copolymer or a block copolymer). Examples of suitable polymers include poly(ethylene oxide), polyethylene glycol, poly(acrylic acid), poly(acrylamide), poly(ethylene imine), poly(vinyl pyrrolidone) and poly(vinyl alcohol).

Preferably the polymeric stabilizer has a weight average molecular weight of at least 1 kDa, more preferably at least 10 kDa, more preferably at least 20 kDa. Preferably, the molecular weight of the polymeric stabilizer is from 1 to 100 kDa, more preferably from 10 to 80 kDa, more preferably from 30 to 60 kDa.

In an embodiment, the polymeric stabilizer is a non-ionic polymer. Examples of non-ionic polymers include, without limitation, poly(vinyl alcohol), poly(vinyl propylene), poly (ethylene glycol) and poly(vinyl pyrrolidone). Poly(vinyl pyrrolidone) is particularly preferred as a steric stabilizer.

In an embodiment, the polymeric stabilizer is a cationic polymer. Examples of cationic polymers include, without limitation, poly(allyl amine) polymers, e.g. poly(allyl amine) hydrochloride).

In an embodiment, the polymeric stabilizer is an anionic polymer. Examples of anionic polymers include, without limitation, polyacids, e.g. poly(acrylic acid) or poly(methacrylic acid).

In an embodiment, the polymeric stabilizer is selected from poly(vinyl alcohol) (PVA), poly(vinyl pyrrolidone) (PVP), poly(acrylic acid) (PAA), poly(methacrylic acid) (PMA) and poly(ethylene glycol). More preferably, the polymeric stabilizer is poly(vinyl pyrrolidone) (PVP).

In an embodiment, the polymeric stabilizer is selected from polyoxyalkylene glycol alkyl ethers (e.g. polyoxyethylene glycol alkyl ethers and polyoxypropylene glycol alkyl ethers), sorbitan esters (e.g. polysorbates) and poly(isobutenyl) succinic anhydride amine derivatives.

Suitable procedures for preparing sterically-stabilized nanoparticles are known in the art. By way of illustration, sterically-stabilized nanoparticles may be prepared by reducing metal ions in solution in the presence of the stabilizer.

Thus, in an embodiment, the emulsifier is obtained by providing a solution comprising ions of the first metal and the stabilizer, and reducing the ions to form metal particles which are sterically stabilized by the stabilizer. Preferably, the ions of the first metal are present in the solution at a concentration of from 0.01 to 100 mM, e.g. from 0.05 to 50 mM, e.g. from 0.1 to 10 mM. Preferably, the stabilizer is present in the solution at a concentration of from 0.0001 to 50 mM, e.g. from 0.01 to 10 mM, e.g. from 0.05 to 5 mM.

The emulsifier comprising the sterically-stabilized nanoparticles may then be used to prepare the emulsion droplet using the procedures described elsewhere herein.

Deposition of the First Metal: Adsorption of Metal Particles onto the Emulsion Droplet In another embodiment, the emulsion droplet is contacted with particles of the first metal such that the particles are adsorbed onto the emulsifier of the emulsion droplet. The particles of the first metal may be bound to the emulsifier in various ways, such as via steric and/or electrostatic interactions. In an embodiment, the particles of the first metal are bound to the emulsifier via electrostatic interactions.

Preferably, the nanoparticles of the first metal are charge-stabilized nanoparticles. Charge-stabilized nanoparticles are nanoparticles which comprise a charged species adsorbed on the surface thereof. Since the stabiliser is a charged species, it will impart a charged surface to the nanoparticles which can be exploited in order to adsorb the metal particles to the emulsifier of the emulsion droplet. Thus, in a preferred embodiment, the nanoparticles of the first metal are adsorbed on the emulsifier of the emulsion droplet by electrostatic interaction. The emulsifier preferably presents a charged surface which is used to electrostatically attract and adsorb the charge-stabilised nanoparticles on to the emulsion droplet.

In a preferred embodiment, the nanoparticles of the first metal are charge-stabilized by an anionic stabilizer. In an embodiment, the anionic stabilizer is selected from borohydride anions and citrate anions. In another embodiment, the anionic stabilizer is an anionic surfactant, e.g. an anionic surfactant selected from sodium dodecyl sulfate, sodium laureth sulfate, dodecyl benzene sulfonic acid, perfluorooctanesulfonate, dioctyl sodium sulfosuccinate and sodium stearate. Preferably, the particles are borohydride-stabilized or citrate-stabilized particles.

In an embodiment, the nanoparticles of the first metal have a zeta potential of from −20 mV to −150 mV. e.g. from −30 mV to −90 mV.

Where the nanoparticles of the first metal are stabilized by an anionic stabilizer, it is preferable for the surface of the emulsion droplet to be neutral or cationic. In an embodiment, the emulsion droplet has a substantially neutral surface having a zeta potential of from −10 mV to +10 mV, e.g. from −5 mV to +5 mV. In an embodiment, the emulsion droplet has a positively charged surface, e.g. having a zeta potential of from +20 mV to +150 mV, e.g. from +30 mV to +90 mV.

In an embodiment, the nanoparticles of the first metal are stabilized by an anionic stabilizer and the emulsifier is a polymeric emulsifier.

In a preferred embodiment, the emulsifier is block copolymer comprising a hydrophilic block and a hydrophobic block. Where the liquid core material comprises a perfume oil or other hydrophobic material, the hydrophobic block of the copolymer may extend, partly or wholly, into the liquid core material, whereas the hydrophilic block may be present at the surface of the emulsion droplet. In this case, the nanoparticles of the first metal will preferably be adsorbed on the hydrophilic block of the polymer.

Preferably, the emulsifier is a di-block copolymer formed of a first block comprising a poly(aminoalkyl acrylate) and a second block comprising a poly(alkyl acrylate). In particular, the emulsifier may be a poly(butylacrylate)-b-(trimethylaminoethyl methacrylate) diblock copolymer.

In an embodiment, the nanoparticles of the first metal are stabilized by an anionic stabilizer and the emulsion droplet comprises a non-ionic emulsifier. In an embodiment, the emulsifier is a non-ionic polymer, e.g. a non-ionic polymer selected from poly(vinyl alcohol) and poly(vinyl pyrrolidone).

In an embodiment, the nanoparticles of the first metal are stabilized by an anionic stabilizer and the emulsion droplet comprises a cationic emulsifier. Examples of cationic emulsifiers include, without limitation, alkyl ammonium surfactants such as cetyl trimethylammonium bromide, dodecyl dimethylammonium bromide, cetyl trimethylammonium chloride, benzalkonium chloride, cetylpyridinium chloride, dioctadecyl dimethylammonium chloride and dioctadecyl dimethylammonium bromide.

In an embodiment, the emulsifier is a cationic polymer. Examples of cationic polymers include, without limitation, poly(diethylaminoethyl methacrylate), poly(dimethylaminoethyl methacrylate), poly(tertiarybutylaminoethyl methacrylate) and di-block copolymers formed of a first block comprising a poly(aminoalkyl acrylate) and a second block comprising a poly(alkyl acrylate) such as poly(butylacrylate)-b-(trimethylaminoethyl methacrylate). In a preferred embodiment, the emulsifier is di-block copolymer formed of a first block comprising a poly(aminoalkyl acrylate) and a second block comprising a poly(alkyl acrylate).

Alternatively, the nanoparticles of the first metal may be charge-stabilized by a cationic stabilizer. Examples of cationic stabilizers include cationic surfactants such as quaternary ammonium surfactants, e.g. cetyl trimethylammonium bromide, tetraoctylammonium bromide and dodecyl trimethylammonium bromide. Other quaternary ammonium surfactants include the esterquats, i.e. quaternary ammonium surfactants containing an ester group.

In an embodiment, the nanoparticles of the first metal have a zeta potential of from +20 mV to +150 mV, e.g. from +30 mV to +90 mV.

Where the nanoparticles of the first metal are stabilised by a cationic stabilizer, it is preferable for the surface of the emulsion droplet to be neutral or anionic. In an embodiment, the emulsion droplet has a substantially neutral surface having a zeta potential of from −10 mV to +10 mV, e.g. from −5 mV to +5 mV. In an embodiment, the emulsion droplet has a positively charged surface, e.g. having a zeta potential of from −20 mV to −150 mV, e.g. from −30 mV to −90 mV.

In an embodiment, the nanoparticles of the first metal are stabilized by a cationic stabilizer and the emulsion droplet comprises a non-ionic emulsifier. In an embodiment, the emulsifier is a non-ionic polymer, e.g. a non-ionic polymer selected from poly(vinyl alcohol) and poly(vinylpyrrolidone).

In an embodiment, the nanoparticles of the first metal are stabilized by a cationic stabilizer and the emulsion droplet comprises an anionic emulsifier. Examples of anionic emulsifiers include, without limitation, sodium dodecyl sulfate, sodium laureth sulfate, dodecyl benzene sulfonic acid, dioctyl sodium sulfosuccinate, perfluorooctanesulfonate, dioctyl sodium sulfosuccinate and sodium stearate. In an embodiment, the emulsifier is an anionic polymer. Examples of anionic polymers include, without limitation, polyacids such as poly(acrylic acid) and poly(methacrylic acid).

The nanoparticles of the first metal may alternatively be charge-stabilized by a zwitterionic stabilizer. In an embodiment, the zwitterionic stabilizer is a zwitterionic surfactant. Examples of zwitterionic surfactants include aminobetaines, imidazoline derivatives and phospholipids, e.g. phosphatidyl cholines.

The charge-stabilized nanoparticles may be prepared using suitable procedures known in the art. Such procedures will typically involve reducing metal ions in solution in the presence of charged stabilizer. Thus, the charge-stabilized nanoparticles may be obtained by providing a solution comprising ions of the first metal and a charged stabilizer, and reducing the ions to form metal nanoparticles which are charge-stabilized by the stabilizer.

In an embodiment, metal ions in solution are reduced by a reducing agent which becomes the charged stabilizer e.g. by sodium borohydride or by sodium citrate. By way of illustration, and without limitation, borohydride-stabilized gold nanoparticles may be prepared by contacting an aqueous solution of chloroauric acid with sodium borohydride.

Preferably, the ions of the first metal are present in the solution at a concentration of from 0.005 to 50 mM. e.g. from 0.01 to 20 mM. e.g. from 0.05 to 5 mM. Preferably, the charged stabilizer is present in the solution at a concentration of from 0.005 to 50 mM, e.g. from 0.01 to 20 mM, e.g. from 0.05 to 5 mM.

The resulting charge-stabilised nanoparticles may then be contacted with emulsion droplets under appropriate conditions, e.g. at ambient temperature.

Deposition of the Second Metal

The metallic film can be formed by depositing a layer of a second metal on the particles of the first metal, thereby forming a metallic film that encapsulates the emulsion droplet. Preferably the metallic film is continuous and surrounds the emulsion droplet. Preferably the thickness of the metallic film is substantially uniform throughout the film.

The metallic film is preferably formed by an electroless plating process in which the deposition of the second metal is catalyzed by the particles of the first metal. The electroless deposition process will generally comprise contacting emulsion droplets onto which particles of the first metal have been deposited with a solution of ions of the second metal in the presence of a reducing agent, in the absence of an electric current. The reducing agent is typically a mild reducing agent such as formaldehyde and the electroless plating is preferably performed under alkaline conditions. Once the electroplating reaction commences, the deposition of the layer of the second metal may become autocatalytic. The thickness of the metallic film may be controlled by limiting the concentration of the ions of the second metal in solution and/or the duration of the electroless plating procedure.

Suitable techniques for conducting the electroless plating procedure are well known.

By way of illustration, and without limitation, a silver film may be prepared by forming a dispersion comprising silver nitrate, formaldehyde, ammonia and emulsion droplets comprising particles of the first metal. The dispersion is then stirred for a sufficient period of time until a metallic film of the desired thickness is obtained. The capsules may then be washed, e.g. by centrifugation, in order to separate them from the plating solution.

The ions of the second metal are preferably present in the solution at a concentration of from 0.05 to 2000 mM, e.g. from 0.1 to 1750 mM, e.g. from 0.5 to 1500 mM. Preferably, the reducing agent is present in the solution at a concentration of from 0.05 to 3500 mM, e.g. from 0.1 to 3000 mM, e.g. from 0.5 to 2500 mM. Preferably, the second metal and the reducing agent are present in the solution at a molar ratio of second metal to reducing agent of from 1:10 to 4:1, e.g. from 1:5 to 2:1, e.g. from 1:3 to 1:1.

The electroless plating process may be performed at any suitable temperature, e.g. a temperature of from 0 to 80° C. Preferably, the electroless plating process is performed at room temperature.

The metallic film may be coated with a polymer film. The polymer film serves to strengthen the microcapsule. The polymer film may comprise polymers which have an affinity for the metallic film. Examples of suitable polymers include poly(vinyl pyrrolidone), poly(acrylic acid), poly(methacrylic acid) and polypyrrole. Other commercially available polymers with an affinity for the metallic film may also be used. The metallic film may be coated with the polymer film by adsorbing a polymer onto the surface of the metallic film, e.g. by adsorbing a polymer which is soluble or partially soluble in an aqueous phase onto the surface of the metallic film when the microcapsules are in an aqueous suspension. In view of the foregoing, the microcapsules may further comprise a polymer film at least partially over coating, preferably completely over coating, the metallic film, preferably the polymer film comprising a polymer selected from poly(vinyl pyrrolidone), poly(acrylic acid), poly(methacrylic acid), polypyrrole, and combinations thereof. Without wishing to be bound by theory, coating the metallic film with the polymer film may increase the robustness of the microcapsules during processing and/or during consumer product use (e.g., providing long lasting freshness when the liquid core material is a perfume). The increased robustness may be evidenced by higher fracture strength values (as previously described). Preferably, these coated microcapsules have a fracture strength from 1 MPa to 10 MPa.

Compositions/Articles

The microcapsules may be included in compositions (i.e. products intended to be sold to consumers without further modification or processing). In some examples, the compositions may include from 0.001% to 99%, by weight of the composition of the microcapsules, alternatively from 0.01% to 90% by weight of the composition of the microcapsules, alternatively from 0.1% to 75% by weight of the composition of the microcapsules, alternatively from 0.1% to 25% by weight of the composition of the microcapsules, alternatively from 1% to 15% by weight of the composition of the microcapsules. The composition may include a mixture of different microcapsules of the present disclosure, the mixture comprising a plurality of microcapsules comprising a first liquid core material and a plurality of microcapsules comprising a second liquid core material. Alternatively or additionally, the composition may comprise other microcapsules, in addition to the microcapsules disclosed herein.

In some examples, the compositions are incorporated into consumer products (i.e. products intended to be sold to consumers without further modification or processing). Moreover, microcapsules may be applied to any article, such as a fabric or any absorbent material including, but not limited to, feminine hygiene products, diapers, and adult incontinence products. The composition may also be included in an article, non-limiting examples of which include a dispenser/container. The compositions/articles disclosed herein may be made by combining the microcapsules disclosed herein with the desired adjunct material to form the consumer product. The microcapsules may be combined with the adjuncts material when the microcapsules are in one or more forms, including a slurry form, neat particle form, and spray dried particle form. The microcapsules may be combined with the adjuncts material by methods that include mixing and/or spraying.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Non-limiting examples of consumer products useful herein include products for treating hair (human, dog, and/or cat), including, bleaching, coloring, dyeing, conditioning, growing, removing, retarding growth, shampooing, styling; deodorants and antiperspirants; personal cleansing; color cosmetics; products, and/or methods relating to treating skin (human, dog, and/or cat), including application of creams, lotions, and other topically applied products for consumer use; and products and/or methods relating to orally administered materials for enhancing the appearance of hair, skin, and/or nails (human, dog, and/or cat); shaving; body sprays; and fine fragrances like colognes and perfumes; products for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps, shampoos, lotions, oral care implements (non-limiting examples including toothpaste, mouth wash, and tooth whitening agents like Crest® Whitestrips®), and clothing; products such as wet or dry bath tissue, facial tissue, disposable handkerchiefs, disposable towels, and/or wipes; products relating to catamenial pads, incontinence pads, interlabial pads, panty liners, pessaries, sanitary napkins, tampons and tampon applicators, and/or wipes.

Personal Care Compositions

In some examples, the consumer product may be a personal care composition, that is, a composition intended to be applied anywhere on the human body and/or articles of clothing for any period of time. Non-limiting examples of personal care compositions include products such as those intended to treat and/or clean hair, styling products, deodorants and antiperspirants, personal cleansing products, cosmetics products, product relating to treating skin such as creams, lotions, and other topically applied products for consumer use; shaving products; hair colouring/bleaching products; body sprays; and fine fragrances like colognes and perfumes. The personal care compositions may be manufactured by any method known in the art and packaged in any dispenser known in the art. In some examples, the personal care composition may include the microcapsules and one or more adjunct materials. In some examples, the personal care compositions include the microcapsules and one or more adjunct materials, wherein the microcapsules comprise at least one perfume oil. In some examples, the personal care composition may include from 0.01% to 20%, by weight of the personal care composition, of microcapsules. Some non-limiting examples of personal care compositions are described in further detail below.

Shampoo Composition

The shampoo composition may comprise one or more detersive surfactants, which provides cleaning performance to the composition. The one or more detersive surfactants in turn may comprise an anionic surfactant, amphoteric or zwitterionic surfactants, or mixtures thereof.

The concentration of the detersive surfactant component in the shampoo composition should be sufficient to provide the desired cleaning and lather performance, and generally ranges from about 2 wt % to about 50 wt %. The shampoo composition may also comprise a shampoo gel matrix, an aqueous carrier, and other additional ingredients described herein.

The shampoo composition may comprise a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from 20 wt % to about 95 wt %, or from 60 wt % to 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

The shampoo composition described herein may comprise a shampoo gel matrix. The shampoo gel matrix comprises (i) from 0.1% to 20% of one or more fatty alcohols, alternative from 0.5% to 14%, alternatively from 1% to 10%, alternatively from about 6% to about 8%, by weight of the shampoo gel matrix; (ii) from 0.1% to 10% of one or more shampoo gel matrix surfactants, by weight of the shampoo gel matrix; and (iii) from 20% to 95% of an aqueous carrier, alternatively from 60% to 85% by weight of the shampoo gel matrix.

The fatty alcohols useful herein are those having from 10 to 40 carbon atoms, from 12 to 22 carbon atoms, from 16 to 22 carbon atoms, or 16 to 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from 20:80 to 80:20 are suitable. The shampoo gel matrix surfactants may be a detersive surfactant.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Conditioner Composition

The conditioner compositions described herein comprise (i) from about 0.025% to about 20%, by weight of the conditioner composition, and (ii) a conditioner gel matrix. After applying to the hair a conditioner composition as described herein, the method then comprises rinsing the conditioner composition from the hair. The conditioner composition also comprises a conditioner gel matrix comprising (1) one or more high melting point fatty compounds, (2) a cationic surfactant system, and (3) a second aqueous carrier.

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amidoamine salt and mono-long alkyl quaternized ammonium salt.

The cationic surfactant system can be included in the composition at a level by weight of from 0.1% to 10%, from 0.5% to 8%, from 0.8% to 5%, and from 1.0% to 4%.

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification. e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from 14 to 30 carbon atoms, from 16 to 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least 90%, and/or at least 95%. These single compounds of high purity provide good rinsability from the hair when the consumer rinses off the composition.

The high melting point fatty compound can be included in the conditioner composition at a level of from 0.1% to 20%, alternatively from 1% to 15%, and alternatively from 1.5% to 8% by weight of the composition, in view of providing improved conditioning benefits such as slippery feel during the application to wet hair, softness and moisturized feel on dry hair.

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from 20 wt % to 95 wt %, or from 60 wt % to 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-on Treatment

The leave-on treatment described herein may comprise from 0.025% to 0.25%, alternatively from 0.05% to 0.2%, alternatively from 0.1% to 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment. The leave-on treatment also comprises (1) one or more rheology modifiers and (2) a third aqueous carrier. The leave-on treatment may also include from 0.025% to 20%, alternatively from 0.05% to 0.5%, alternatively from 0.1% to 1% microcapsules, by weight of the leave-on treatment.

The leave-on treatment may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. In an embodiment, the leave-on treatment may comprise from 0.01% to 3% of a rheology modifier, alternatively from 0.1% to 1% of a rheology modifier, The leave-on treatment may comprise a third aqueous carrier. Accordingly, the formulations of the leave-on treatment can be in the form of pourable liquids (under ambient conditions). Such compositions will therefore typically comprise a third aqueous carrier, which is present at a level of at least 20 wt %, from 20 wt % to 95 wt %, or from 60 wt % to 85 wt %. The third aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The third aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

pH

The shampoo composition, conditioner composition, and/or leave-on treatment may have a pH in the range from 2 to 10, at 25° C. The shampoo composition, conditioner composition, and/or leave-on treatment may have a pH in the range of from 2 to 6, alternatively from 3.5 to 5, alternatively from 5.25 to 7, which may help to solubilize copper and redox metals already deposited on the hair.

Additional Components

The shampoo composition, conditioner composition, and/or leave-on treatment (hair care compositions) described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents (e.g., silicones, hydrocarbon oils, fatty esters), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

Rinse-Off Formulations

The personal care composition may be a rinse-off formulation that can be applied topically to the skin and/or hair and rinsed from the skin and/or hair within minutes with water. The personal care composition may comprise a primary surfactant. Primary surfactants may comprise from 0.1% to 20%, from 2% to 10%, from 5% to 10%, or from 2% to 5% by weight of the personal care composition. The primary surfactant may comprise one or more anionic surfactants. The personal care compositions may also comprise a secondary surfactant. Secondary surfactants may comprise from 0.1% to 20%, from 2% to 10%, or from 2% to 5% by weight of the personal care composition. Secondary surfactants may also comprise more than 20% by weight of the personal care composition. The personal care compositions may also contain from 20% to 95%, from 40% to 90%, from 60% to 90%, or from 70% to 90% of water, by weight of the personal care composition. The personal care compositions may further comprise a viscosity modifier for modifying the viscosity of the personal care composition. Such concentrations of viscosity modifiers may range, for example, from 0.1% to 10%, from 0.3% to 5.0%, from 0.5% to 10%, or from 0.5% to 3% by weight of the personal care compositions. The personal care compositions may also include other personal care adjunct ingredients that may modify the physical, chemical, cosmetic or aesthetic characteristics of the personal care compositions or serve as "active" components when deposited on the skin. Non-limiting examples of primary surfactants include sodium lauryl sulfate, ammonium lauryl sulfate, sodium laureth sulfate, and ammonium laureth sulfate. Non-limiting examples of secondary surfactants include cocamidopropyl betaine. Non-limiting examples of other ingredients include fragrances and polyols. Non-limiting examples of viscosity modifiers include sodium carbonate, sodium chloride, sodium aluminum sulfate, disodium phosphate, sodium polymetaphosphate, sodium magnesium succinate, sodium sulfate, sodium tripolyphosphate, aluminum sulfate, aluminum chloride.

The rinse-off formulation may be a single-phased or a multi-phased product. Multi-phased is meant that at least two phases herein occupy separate, but distinct physical spaces inside the package in which they are stored, but are in direct contact, with another. The multi-phase product may have a cleansing phase and a benefit phase. The cleansing phase may comprise a surfactant component comprising a surfactant or a mixture of surfactants. Non-limiting examples of these surfactants include anionic, nonionic, cationic, zwitterionic, and amphoteric surfactants, soap, and combinations thereof. The benefit phase may be anhydrous. The multi-phase product may also include a non-lathering, structured aqueous phase that comprises a water structurant and water. The single and/or multi-phase product may also include other ingredients, non-limiting examples of which include humectants, occlusive agents, and fragrances.

Body Spray/Fine Fragrance

The personal care composition may be an aerosolized composition (i.e. a composition intended to be aerosolized) like a body spray and/or fine fragrance. The aerosolized compositions described herein may include a volatile solvent or a mixture of volatile solvents. The volatile solvents may comprise greater than or equal to 10%, greater than 30%, greater than 40%, greater than 50%, greater than 60%, or greater than 90%, and less than 99% by weight of the composition. A non-limiting example of a volatile solvent is ethanol. In some examples, the aerosolized composition may comprise from 0.01% to 98%, by weight of the composition, of ethanol. The aerosolized composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof. "Nonvolatile" refers to those materials that are liquid under ambient conditions and which have a measurable vapor pressure at 25° C. These materials typically have a vapor pressure less than about 0.01 mmHg, and an average boiling point typically greater than about 250° C.

The aerosolized composition may also include one or more non-encapsulated fragrances. Generally, the fragrance (s) may be present at a level from 0.01% to 40%, from 0.1% to 25%, from 0.25% to 20%, or from 0.5% to 15%, by weight of the composition. Non-limiting examples of fragrances include alcohols, aldehydes, ketones, ethers, Schiff bases, nitriles, and esters. The compositions described herein may include a carrier. Non-limiting examples of carriers include water, silicone oils like silicone D5, and other oils like mineral oil, isopropyl myristate, and perfume oils. If present, the water may comprise from 0.1% to 40%, from 1% to 30%, or from 5% to 20%, by weight, of the composition. In some examples, the aerosolized composition may include a propellant; non-limiting examples of propellants include compressed air, nitrogen, inert gases, carbon dioxide, gaseous hydrocarbons like propane, n-butane, isobutene, cyclopropane, and mixtures thereof. In some examples, the aerosolized composition is aerosolized by the inherent design of the dispenser, such as by the use of a swirl chamber or other internal design. The aerosolized composition may also include other ingredients; non-limiting examples of which include an antiperspirant active (for use in a body spray) or other materials like colorants (for use in a fine-fragrance). In some examples, the aerosolized composition may be substantially free of a material selected from the group consisting of a propellant, a detersive surfactant, and combinations thereof. In some examples, the aerosolized composition includes one or more suspending agents as disclosed herein. In some examples, the aerosolized composition includes from 50% to 99.9%, by weight of the composition, of ethanol; optionally from 0.5% to 50% by weight of the composition of a fragrance; and optionally from 0.01% to 15% by weight of the composition of a suspending agent.

Antiperspirant/Deodorant

The personal care composition may be an antiperspirant composition/deodorant. The personal care composition may include an antiperspirant active suitable for application to human skin. The concentration of the antiperspirant active in the antiperspirant composition should be sufficient to provide the desired enhanced wetness protection. For example, the active may be present in an amount of from 0.1%, 0.5%, 1%, or 5%; to 60%, 35%, 25% or 20%, by weight of the antiperspirant composition. These weight percentages are calculated on an anhydrous metal salt basis exclusive of water and any complexing agents such as glycine, glycine salts, or other complexing agents. Personal care compositions may also include a structurant to help provide the personal care composition with the desired viscosity, rheology, texture and/or product hardness, or to otherwise help suspend any dispersed solids or liquids within the personal care composition. The term "structurant" may include any material known or otherwise effective in providing suspending, gelling, viscosifying, solidifying, or thickening properties to the personal care composition or which otherwise provide structure to the final product form. Non-limiting examples of structurants include, for example, gelling agents, polymeric or nonpolymeric agents, inorganic thickening agents, or viscosifying agents. The concentration and type of the structurant selected for use in the personal care composition may vary depending upon the desired product form, viscosity, and hardness. The personal care compositions may include a surfactant. A surfactant is generally present at a level of 0.05% to 5%, by weight of the personal care composition, but may contain, from 0.5% to 5.0%; from 1.0% to 4%; from 1.5% to 3.5%; from 1.75% to 2.5%; 2%, or any combination thereof. Personal care compositions may also include anhydrous liquid carriers. The anhydrous liquid carrier may be present, for example, at concentrations ranging from 10%, 15%, 20%, 25%; to 99%, 70%, 60%, or 50%, by weight of the personal care composition. Such concentrations will vary depending upon variables such as product form, desired product hardness, and selection of other ingredients in the personal care composition. The anhydrous carrier may be any anhydrous carrier known for use in personal care compositions or otherwise suitable for topical application to the skin. For example, anhydrous carriers may include, but are not limited to, volatile and nonvolatile fluids. The personal care composition may also include a malodor reducing agent.

Malodor reducing agents include components other than the antiperspirant active within the personal care composition that act to eliminate the effect that body odor has on fragrance display. These agents may combine with the offensive body odor so that they are not detectable including and may suppress the evaporation of malodor from the body, absorb sweat or malodor, mask the malodor, and/or prevent/inhibit microbiological activity from odor causing organisms. The concentration of the malodor reducing agent within the personal care composition should be sufficient to provide such chemical or biological means for reducing or eliminating body odor. Although the concentration will vary depending on the agent used, generally, the malodor reducing agent may be included within the personal care composition from 0.05%, 0.5%, or 1%; to 15%, 10%, or 6%, by weight of the personal care composition. Malodor reducing agents may include, but are not limited to, pantothenic acid and its derivatives, petrolatum, menthyl acetate, uncomplexed cyclodextrins and derivatives thereof, talc, silica and mixtures thereof.

The personal care compositions described herein may include a moisture-triggered fragrance technology delivery system that utilizes cyclic oligosaccharides, starches, starch-derivatives, polysaccharide-based encapsulation systems, and combinations thereof. As used herein, the term "cyclic oligosaccharide" means a cyclic structure comprising six or more saccharide units. The cyclic oligosaccharides may have six, seven, or eight saccharide units or mixtures thereof. It is common in the art to refer to six, seven and eight membered cyclic oligosaccharides as α, β, and γ, respectively. The cyclic oligosaccharides that may be useful include those that are soluble in water, ethanol, or both water and ethanol. The cyclic oligosaccharides useful herein may have a solubility of at least about 0.1 g/100 ml, at 25° C. and 1 atm of pressure in either water, ethanol, or both water and ethanol. The personal care compositions disclosed herein may comprise from 0.001% to 40%, from 0.1% to 25%, from 0.3% to 20%, from 0.5% to 10%, or from 0.75% to 5%, by weight of the personal care composition, of a cyclic oligosaccharide. The personal care compositions disclosed herein may comprise from 0.001% to 40%, from 0.1% to 25%, from 0.3% to 20%, from 0.5% to 10%, or from 0.75% to 5%, by weight of the personal care composition, of a cyclic oligosaccharide.

The personal care compositions may include one or more fragrances. As used herein, "fragrance" is used to indicate any odoriferous material. Any fragrance that is cosmetically acceptable may be used in the personal care composition. For example, the fragrance may be one that is a liquid at room temperature. Generally, the fragrance(s) may be present at a level from 0.01% to 40%, from 0.1% to 25%, from 0.25% to 20%, or from 0.5% to 15%, by weight of the personal care composition. The personal care compositions may also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

Cosmetic Composition

The personal care composition may take the form of a cosmetic composition that may be applied to mammalian keratinous tissue, including human skin. The cosmetic compositions may take various forms. For example, some non-limiting examples of forms include solutions, suspensions, lotions, creams, gels, toners, sticks, pencils, ointments, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

For example, the cosmetic composition may comprise from 1% to 95% by weight of water. The cosmetic composition may comprise from 1% to 95% by weight of one or more oils. Oils may be used to solubilize, disperse, or carry materials that are not suitable for water or water soluble solvents. Suitable oils include silicones, hydrocarbons, esters, amides, ethers, and mixtures thereof. When the cosmetic composition is in the form of an emulsion, oils are carriers typically associated with the oil phase. The cosmetic composition may be in the form of a water-in-oil emulsion, an oil-in-water emulsion, or a water-in-silicone emulsion such that the cosmetic composition may include water, a silicone, oil, and combinations thereof. The cosmetic compositions may include an emulsifier. An emulsifier is particularly suitable when the cosmetic composition is in the form of an emulsion or if immiscible materials are being combined. The cosmetic composition may comprise from 0.05%, 0.1%, 0.2%, 0.3%, 0.5%, or 1% to 20%, 10%, 5%, 3%, 2%, or 1% emulsifier. Emulsifiers may be nonionic, anionic, zwitterionic, or cationic. Structuring agents may be used to increase viscosity, thicken, solidify, or provide solid or crystalline structure to the cosmetic composition. Structuring agents are typically grouped based on solubility, dispersibility, and phase compatibility. Examples of aqueous or water structuring agents include, but are not limited to, polymeric agents, natural or synthetic gums, polysaccharides, and the like. The cosmetic compositions may comprise from 0.0001%, 0.001%, 0.01%, 0.05%, 0.1%, 0.5%, 1%, 2%, 3%, 5% to 25%, 20%, 10%, 7%, 5%, 4%, or 2%, by weight of the cosmetic composition, of one or more structuring agents. The cosmetic compositions may optionally contain one or more UV actives. As used herein, "UV active" includes both sunscreen agents and physical sunblocks. Suitable UV actives may be organic or inorganic. Examples of some suitable UV actives are listed in the functional category of "Sunscreen Agents" in the Personal Care Product Council's *International Cosmetic Ingredient Dictionary and Handbook*, Thirteenth Edition, 2010. The cosmetic compositions may be generally prepared by conventional methods such as those known in the art of making cosmetic compositions. Such methods typically involve mixing of ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The cosmetic compositions are preferably prepared such as to optimize stability (physical stability, chemical stability, photostability, etc.) and/or delivery of active materials. The cosmetic composition may be provided in a package sized to store a sufficient amount of the cosmetic composition for a treatment period. The size, shape, and design of the package may vary widely.

The cosmetic compositions disclosed herein may be applied to one or more skin surfaces and/or one or more mammalian keratinous tissue surfaces as part of a user's daily routine or regimen. Additionally or alternatively, the cosmetic compositions herein may be used on an "as needed" basis. In some examples, an effective amount of the cosmetic composition may be applied to the target portion of the keratinous tissue or skin. In some examples, the cosmetic composition may be provided in a package with written instructions detailing the application regimen.

Hair Colouring/Bleaching Composition

In some examples, the microcapsules may be incorporated into personal care composition that is a hair coloring and or bleaching composition. Such hair coloring compositions often are provided as a two part form comprising a first component comprising the oxidizing agent and a second component comprising a surfactant system and if present dyes, wherein the first and second component are mixed together prior to the application of the resultant composition onto the hair of the consumer. The microcapsules disclosed herein may be used to encapsulate one or more actives in order to provide a 1 part form comprising a first component comprising the oxidizing agent and a second component comprising a surfactant system and if present dyes, wherein at least one of the oxidizing agent, surfactant system, and dye is encapsulated using the microcapsules disclosed herein. In some examples, the oxidizing agent (e.g. inorganic peroxygen material capable of yielding hydrogen peroxide in aqueous solution) is encapsulated in the microcapsules and included in the hair coloring/bleaching composition. In other examples, one or more adjunct materials are encapsulated within the microcapsules in order to provide a 1 part form.

Non-limiting examples of adjunct materials for hair coloring/bleaching compositions include oxidizing agents such as water-soluble peroxygen oxidizing agents; alkyl glucosides such as a $C_6$ to $C_{16}$ alkyl glucoside which is comprised within the first or developer composition according to the formula R1-O-(G)x-H wherein R1 is a linear or branched alkyl or alkenyl group comprising from 6 to 16 carbon atoms; associative polymers such as acrylic acid, methacrylic acid or itaconic acid; surfactants such as alkyl ether phosphates having an average of 1 to 20 ethylene oxide units; oxidative dye precursors or developers; non-oxidative pre-formed dyes; carbonate ion sources; additional thickeners and/or rheology modifiers; solvents; radical scavenger; enzymes, additional surfactants; conditioning agents; carriers; antioxidants; stabilizers; chelants; perming actives; perfume; pearling agents; opacifiers; fluorescent dyes; reducing agents (thiolactic acid); hair swelling agents and/or polymers; gel network thickeners; cationic polymers such as polyquaternium 37, polyquaternium 7, polyquaternium 22, polyquaternium 87 and mixtures thereof; alkalizing agents such as those that provide a source of ammonium ions; couplers like phenols; direct dyes like acid yellow 1; conditioning agents like silicones; radical scavengers like monoethanolamine; chelants like EDDS (ethylenediaminedisuccinic acid); solvents like water; and mixtures thereof.

Any oxidizing agent known in the art may be utilized. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can be used if desired. The oxidizing agents may be provided in aqueous solution or as a powder which is dissolved prior to use. In some examples, the oxidizing agent is encapsulated within the coated particles. Non-limiting examples of preferred oxidizing agents are hydrogen peroxide, percarbonate (which may be used to provide a source of both oxidizing agent and carbonate ions), persulphates and combinations thereof.

Suspending Agents

The compositions described herein may include one or more suspending agents to suspend the microcapsules and other water-insoluble and/or ethanol-insoluble material dispersed in the composition. The concentration of the suspending agent may range from 0.01% to 90%, alternatively from 0.01% to 15% by weight of the composition, alternatively from 0.1% to 15%.

Non-limiting examples of suspending agents include anionic polymers, cationic polymers, and nonionic polymers. Non-limiting examples of said polymers include vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate and alginic acid, propylene glycol esters, acrylate polymers such as sodium polyacrylate, polyethylacrylate, polyacrylamide, and polyethyleneimine, and inorganic water soluble material such as bentonite, aluminum magnesium silicate, laponite, hectonite, and anhydrous silicic acid. Other suspending agents may include, but are not limited to, Konjac, Gellan, and a methyl vinyl ether/maleic anhydride copolymer crosslinked with decadiene (e.g. Stabileze®).

Other non-limiting examples of suspending agents include cross-linked polyacrylate polymers like Carbomers with the trade names Carbopol® 934, Carbopol® 940, Carbopol® 950, Carbopol® 980, Carbopol® 981, Carbopol® Ultrez 10, Carbopol® Ultrez 20, Carbopol Ultrez 21, Carbopol® Ultrez 30, Carbopol® ETD2020, Carbopol® ETD2050, Pemulen® TR-1, and Pemulen® TR-2, available from The Lubrizol Corporation; acrylates/steareth-20 methacrylate copolymer with trade name ACRYSOL™ 22 available from Rohm and Hass; acrylates/beheneth-25 methacrylate copolymers, trade names including Aculyn-28 available from DOW, and Volarest™ FL available from Croda; acrylates copolymers with the trade name Aculyn 33 available from DOW; Peg-150/Decyl Alcohol/Smdi Copolymer with the trade name Aculyn 44 available from DOW; nonoxynyl hydroxyethylcellulose with the trade name Amercell™ POLYMER HM-1500 available from Amerchol; methylcellulose with the trade name BENECEL®, hydroxyethyl cellulose with the trade name NATROSOL®; hydroxypropyl cellulose with the trade name KLUCEL®; cetyl hydroxyethyl cellulose with the trade name POLYSURF® 67, supplied by Hercules; ethylene oxide and/or propylene oxide based polymers with the trade names CARBOWAX® PEGs, POLYOX WASRs, and UCON® FLUIDS, all supplied by Amerchol; ammonium acryloyl dimethyltaurate/carboxyethyl-acrylate-crosspolymers like Aristoflex® TAC copolymer, ammonium acryloyl dimethyltaurate/VP copolymers like Aristoflex® AVS copolymer, sodium acryloyl dimethyltaurate/VP crosspolymers like Aristoflex® AVS copolymer, ammonium acryloyl dimethyltaurate/beheneth-25 methacrylate crosspolymers like Aristoflex® BVL or HMB, polyacrylate crosspolymer-11 like Aristoflex Velvet, all available from Clariant Corporation; polyacrylate crosspoylmer-6 with the trade name Sepimax™ Zen, available from Seppic; and cross-linked copolymers of vinyl pyrrolidone and acrylic acid such as UltraThix™ P-100 polymer available from Ashland.

Other non-limiting examples of suspending agents include crystalline suspending agents which can be categorized as acyl derivatives, long chain amine oxides, and mixtures thereof.

Other non-limiting examples of suspending agents include ethylene glycol esters of fatty acids, in some aspects those having from 16 to 22 carbon atoms; ethylene glycol stearates, both mono and distearate, in some aspects, the distearate containing less than about 7% of the mono stearate; alkanol amides of fatty acids, having from 16 to 22 carbon atoms, or 16 to 18 carbon atoms, examples of which include stearic monoethanolamide, stearic diethanolamide, stearic monoisopropanolamide and stearic monoethanolamide stearate; long chain acyl derivatives including long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin), a commercial example of which is Thixin® R available from Rheox, Inc. Other non-limiting examples of suspending agents include long chain acyl derivatives, ethylene glycol esters of long chain carboxylic acids, long chain amine oxides, and alkanol amides of long chain carboxylic acids.

Other non-limiting examples of suspending agents include long chain acyl derivatives including N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Non-limiting examples of suitable long chain amine oxides for use as suspending agents include alkyl dimethyl amine oxides (e.g., stearyl dimethyl amine oxide).

Other non-limiting suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow) amine. Other non-limiting examples of suspending agents include di(hydrogenated tallow)phthalic acid amide, and cross-linked maleic anhydride-methyl vinyl ether copolymer.

Fabric and Home Care Compositions

In some examples, the microcapsules are included in a fabric and home care product. As used herein, the term "fabric and home care product" is a cleaning and treatment composition that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which are applicable may be in standard, concentrated or even highly concentrated form even to the extent that such products may in certain aspect be non-aqueous.

The non-limiting list of adjuncts materials illustrated hereinafter are suitable for use in compositions and may be desirably incorporated in certain aspects, for example to assist or enhance cleaning performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the fabric treatment operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents and/or pigments.

As stated, the adjunct ingredients are not necessarily essential. Thus, certain aspects of Applicants' compositions do not contain one or more of the following adjuncts materials: surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems structure elasticizing agents, carriers, hydrotropes, processing aids, solvents and/or pigments.

Packaging

The microcapsules may be stored in any container or dispenser known in the art.

Method of Use

The personal care compositions disclosed herein may be applied to one or more skin surfaces and/or one or more mammalian keratinous tissue surfaces as part of a user's daily routine or regimen. Additionally or alternatively, the compositions herein may be used on an "as needed" basis and used for as intended for the given consumer product. The composition may be applied to any article, such as a textile, or any absorbent article including, but not limited to, feminine hygiene articles, diapers, and adult incontinence articles. For example, the compositions may be used as a body lotion, body spray, feminine spray, adult incontinence spray, baby spray, fine fragrance spray, or other spray. The size, shape, and aesthetic design of the dispensers described herein may vary widely as may the mechanical design of the dispenser.

Characteristics and Properties of the Microcapsules

The microcapsules of the present invention may be obtained in a range of different particle sizes. Preferably, the microcapsules have a particle size of at least 0.1 microns, more preferably at least 1 micron. Typically, the microcapsules will have particle size of 500 microns or less, such as 100 microns or less, and more preferably 50 microns or less. Preferably, the microcapsules have a particle size of from 0.1 to 500 microns, e.g. from 1 to 100 microns, e.g. from 1 to 30 microns. e.g. from 1 to 20 microns. The particle size of the microcapsules may be determined using the test procedure described in the Test Methods section herein.

The thickness of the metallic film may be chosen such that the microcapsules rupture and release the encapsulated liquid core material under particular conditions, e.g. under particular stresses. For instance, when the microcapsules comprise a perfume oil and form part of a fragrance formulation that is worn by a user, the metallic film may rupture during use, e.g. due to rubbing of the skin to which the formulation has been applied. In this way, the perfume oil may be released in a controlled manner so that it is perceptible to the user for a prolonged period of time.

Conversely, it is also desirable for the metallic film to have a minimum thickness so as to reduce the likelihood of solvents permeating there through and/or the metallic film rupturing prematurely when the microcapsules are stored, transported or used. This is particularly important in the case of fine fragrance formulations, which will typically comprise a polar solvent such as ethanol in which the microcapsules are dispersed.

In an embodiment, the metallic film has a maximum thickness of 1000 nm, e.g. a maximum thickness of 500 nm, e.g. a maximum thickness of 400 nm e.g. a maximum thickness of 300 nm, e.g. a maximum thickness of 200 nm, e.g. a maximum thickness of 150 nm, e.g. a maximum thickness of 100 nm, e.g. a maximum thickness of 50 nm. In an embodiment, the metallic film has a minimum thickness of 1 nm, e.g. a minimum thickness of 10 nm, e.g. a minimum thickness of 30 nm. In some embodiments, the metallic film has: a minimum thickness of 1 nm and a maximum thickness of 500 nm; a minimum thickness of 10 nm and a maximum thickness of 300 nm; or a minimum thickness of 10 nm and a maximum thickness of 200 nm. Preferably, the metallic film has: a minimum thickness of 10 nm and a maximum thickness of 150 nm; a minimum thickness of 10 nm and a maximum thickness of 100 nm; a minimum thickness of 20 nm and a maximum thickness of 100 nm. Preferably the thickness of the metallic film is substantially uniform throughout the film.

The microcapsules are designed to release their liquid core material when the microcapsules are ruptured. The rupture can be caused by forces applied to the microcapsules during mechanical interactions. The microcapsules may have a fracture strength of from about 0.1 MPa to about 25 MPa. The microcapsules preferably have a fracture strength of at least 0.5 MPa. So that the microcapsules are readily friable, they preferably have a fracture strength of less than 25 MPa, more preferably of less than 20 MPa, more preferably of less than 15 MPa. For instance, the microcapsules may have a fracture strength of from 0.5 to 10 MPa. The fracture strength of the microcapsules may be measured according to the Fracture Strength Test Method described in WO 2014/047496 (see pages 28-30 thereof).

The microcapsules may be characterized in terms of their permeability. A microcapsule of the present invention preferably retains more than 50% by weight of the liquid core material under the Ethanol Stability Test described herein. More preferably, the microcapsule preferably retains more than 70% by weight of the liquid core material, e.g. more than 80% by weight, e.g. more than 85% by weight, e.g. more than 90% by weight, e.g. more than 95% by weight, e.g. more than 98% by weight, when tested under the Ethanol Stability Leakage Test described herein.

Formulations and Uses

The microcapsules of the present invention will typically be formulated as a plurality of microcapsules. Thus, in one aspect, the present invention provides a formulation comprising a plurality of microcapsules of the present invention. The microcapsules will typically be dispersed in a solvent. For example, the microcapsules may be dispersed in water or a polar solvent, e.g. an alcohol such as ethanol.

Preferably, the formulation comprises the microcapsules in an amount of at least 1% by weight of the formulation. For example, the microcapsules may be present in an amount of at least 5% by weight, at least 7% by weight, at least 10% by weight, at least 20% by weight or at least 50% by weight of the formulation. The formulation may comprise a mixture of different microcapsules of the present invention, the mixture comprising a plurality of microcapsules comprising a first liquid core material and a plurality of microcapsules comprising a second liquid core material. Alternatively or additionally, the formulation may comprise other encapsulated liquid cores in addition to the microcapsules of the present invention.

Preferably, at least 75%, 85% or even 90% by weight of the microcapsules in the formulation have a particle size of from 1 microns to 100 microns, more preferably from 1 microns to 50 microns, even more preferably from 10 microns to 50 microns, most preferably from 1 microns to 30 microns.

The microcapsules may be used in a wide variety of consumer products. Thus, the microcapsules may be used in products for baby care, beauty care, fabric care, home care, family care, feminine care or health care.

Preferably, the microcapsules are used in topically applied products, including fine fragrances and skin care products, including shaving products. Other examples of consumer products where the microcapsules may find application include diapers, bibs, wipes; products for treating hair, including, bleaching, coloring, dyeing, conditioning, shampooing and styling products; deodorants and antiperspirants; personal cleansing products; cosmetics; products for treating fabrics, hard surfaces and any other surfaces in the area of fabric and home care, including air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products relating to bath tissue, facial tissue, paper handkerchiefs, and/or paper towels; tampons; feminine napkins; products relating to oral care including toothpastes, tooth gels, tooth rinses, denture adhesives, tooth whitening; medicinal products; and veterinary products.

In one embodiment, the present invention provides a product for topical use which comprises a plurality of microcapsules of the present invention. Examples of such products include fine fragrances and skin care products, including skin care products which are applied as a cream, gel, lotion or foam.

In particular, the present invention provides a fragrance formulation which comprises a plurality of microcapsules of the present invention, the microcapsules comprising a liquid core material comprising a perfume oil. The formulation will typically comprise a polar solvent in which the microcapsules are dispersed. Preferably the polar solvent is ethanol. Thus, in a particular embodiment, the present invention provides a fragrance formulation comprising a plurality of microcapsules of the present invention dispersed in ethanol. More preferably, the fragrance formulation is a fine fragrance formulation.

Test Methods

Test Method for Measuring the Size of/Characterizing the Emulsion Droplets

The size and shape of the emulsion droplets may be measured using a Malvern Sysmex FPIA-2100 image analysis instrument. Measurements are performed using: Number Base analysis, a circularity of <0.95, a measurement mode of LPF→HPH, a dispersant, and a particle sheath.

Test Method for Measuring the Size of the Microcapsules

The dimensions of microcapsules may be measured using a Malvern Mastersizer Hydro 2000SM particle size analyzer. Measurements are performed according to British Standard BS ISO 13099-1:2012 ("Colloidal systems—Methods for zeta-potential determination").

Test Method for Measuring the Size of the Metal Particles

The dimensions of metal particles may be measured by electron microscopy. Specifically, an FEI Tecnai TF20 field emission gun transmission electron microscope (FEGTEM) fitted with HAADF detector and Gatan Orius SC600A CCD camera may be used.

Test Method for Measuring the Thickness of the Metallic Film

The thickness of the metallic film may be measured using microtoming and FEGTEM. In order to prepare capsule cross-section samples for TEM imaging, 1% of the washed capsules are centrifuged and redispersed in 1 mL of ethanol. The capsule samples are then air dried and mixed with EPO FIX epoxy resin. The sample is left to harden overnight and ~100 nm thick microtome samples are floated onto water and set on TEM grids. FEGTEM is used to generate images of the microtomes and the thickness of the metallic film may be determined using a computer program, such as Image J.

The thickness of the metallic film can be measured using thermogravimetric analysis (TGA). It can be used to measure the mass ratio of the emulsion droplets before and after the secondary metal is deposited. Using size distribution of the uncoated emulsion droplets, the thickness of the second metallic film can be determined from the mass change.

Test Method for Measuring the Adsorption Density of Metal Particles on the Emulsion Droplet Surface Metal particle surface adsorption densities may be derived from thermogravimetric analysis (TGA) of an emulsion comprising particles of the first metal and the emulsion droplets. Specifically. TGA may be used to measure the weight ratio of the particles of the first metal to the oil core. Using measurements on the size distribution of the emulsion droplets, the particle surface adsorption density may be determined.

To quantify the proportion of metal particles adsorbed from the continuous phase of the emulsion onto the surface of the emulsion droplet, transmission of the continuous phase of the emulsion may be recorded using Fullbrook Turbiscan™ LAB Analyser. The concentration of particles in the continuous phase of the emulsion may be deduced from a calibration curve of transmission at different particle concentrations. Once the concentration of particles in the continuous phase is known, the mass of the particles that have adsorbed from the continuous phase onto the surface of the emulsion droplet may be calculated. This method can also be carried out using a LUM LUMiSizer or UV-vis spectrophotometer. Absorbance measurements are recorded for the UV-vis spectrophotometer (and the respective calibration)

Test Method for Measuring Zeta Potentials

The zeta potentials of the metal particles, emulsion droplets and microcapsules may be analyzed using a Malvern nano-ZS zetasizer. Zeta potentials are measured according to British Standard BS ISO 13099-1:2012 ("Colloidal systems—Methods for zeta-potential determination").

Test Method for Analyzing the Chemical Composition of the Microcapsules

The chemical composition of the microcapsules may be analyzed using an Oxford Instruments INCA 350 energy dispersive X-ray spectroscopy (EDX) with 80 mm X-Max SDD detector, which is installed in FEGTEM; and EDX in FEGTSEM.

Ethanol Stability Test

The Ethanol Stability Test refers to the following test procedure.

A known volume of microcapsules are isolated and dispersed in an aqueous solution consisting of 1 part water to 4 parts absolute ethanol. The dispersion is heated to 40° C. After 7 days at 40° C., the microcapsules are isolated from the aqueous solution using centrifugation at 7000 rpm for 1 minute.

The aqueous solution is then subjected to analysis using gas chromatography to determine the content of the liquid core material that has leached from the microcapsules. Samples are assessed using a fused silica column of 3 m in length and 0.25 mm internal diameter, coated with a 0.25 mm film of 100% dimethyl polysiloxane stationary phase. The column temperature is programmed to increase from 50° C. to 300° C. at a rate of 20° C. per minute. A Clarus 580 gas chromatograph is used for the analysis.

To confirm the presence of the liquid core material within the microcapsules, a known sample of capsules is crushed between two glass slides and washed into a vial with 5 ml ethanol. The capsules are isolated from the aqueous solution using centrifugation at 7000 rpm for 1 minute. The aqueous solution is then subjected to analysis using gas chromatography to determine the content of the liquid core material that has leached from the microcapsules.

The following Examples describe and illustrate embodiments within the scope of the present invention. The Examples are given solely for the purpose of illustration and are not to be construed as limitations of the present invention, as many variations thereof are possible without departing from the spirit and scope of the invention.

Unless otherwise stated, the test procedures used in these Examples are those specified in the Test Methods section of this specification.

Example 1: Preparation of a Pt-PVP Emulsifier

The following procedure was used to prepare an emulsifier comprising platinum nanoparticles sterically stabilized by a poly(vinyl pyrrolidone) stabilizer.

Poly(vinyl pyrrolidone) (PVP, 40 kDa, Fluka) was dissolved in Milli-Q water to give a 0.00625 wt % solution of PVP. 0.23 g of $H_2PtCl_6 \cdot 6H_2O$ (≥99.9%, Aldrich) was added to 100 ml of this PVP solution and stirred to dissolve. A 1.1 mM solution of $NaBH_4$ (≥98.0%, Aldrich) was made by dissolving $NaBH_4$ in Milli-Q water. 1 ml of this was added to the platinum salt-PVP solution at room temperature with stirring at 900 rpm for 5 minutes. The solution turned dark brown and was left to stand at room temperature for one day to form Pt-PVP nanoparticles.

Example 2: Preparation of Emulsion Droplets Comprising a Pt-PVP Emulsifier and a Hexadecane Core The following procedure was used to prepare emulsion droplets comprising a Pt-PVP emulsifier disposed around a hexadecane core. The emulsion droplets were prepared by oil-in-water emulsification.

0.1 ml of hexadecane (99%, Aldrich) was added to 20 ml of the Pt-PVP dispersion of Example 1. The mixture was emulsified using a homogenizer (IKA T25 Ultra-Turrax) at 24000 rpm for 2 min. The resulting emulsion was agitated on a carousel for 30 minutes. Once a fully creamed emulsion was obtained, the emulsion was washed with Milli-Q water four times.

Figure 3A:
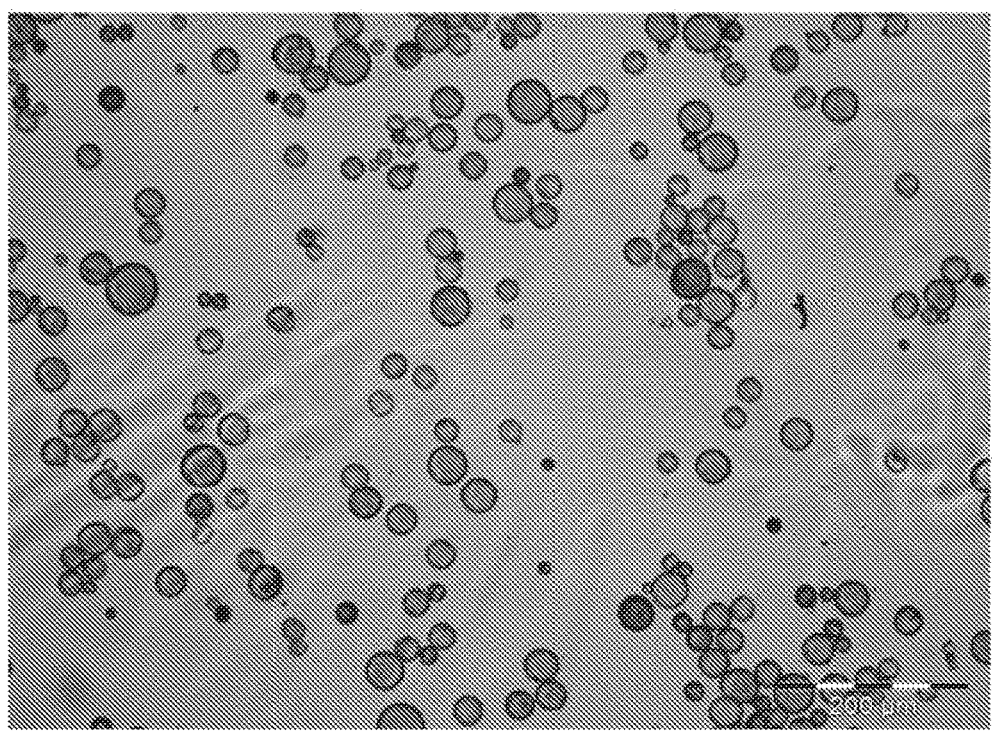
FIGS. 3a and 3b are optical micrographs showing emulsion droplets comprising a Pt-PVP emulsifier and a hexadecane core.
Figure 3B:
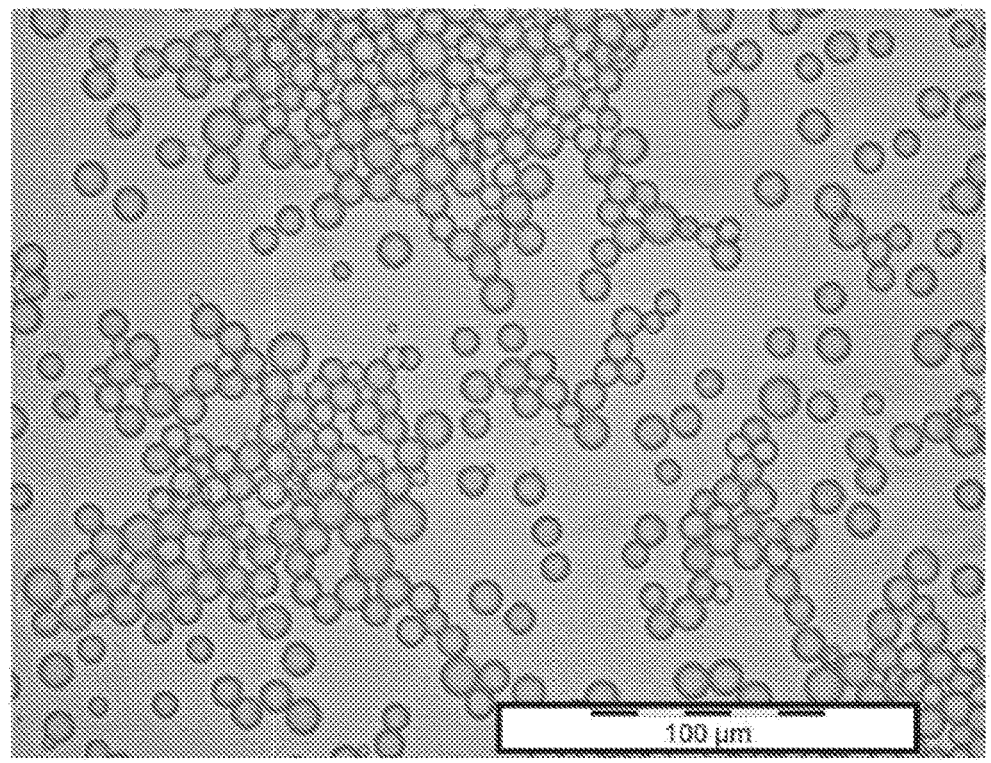
Figure 4:
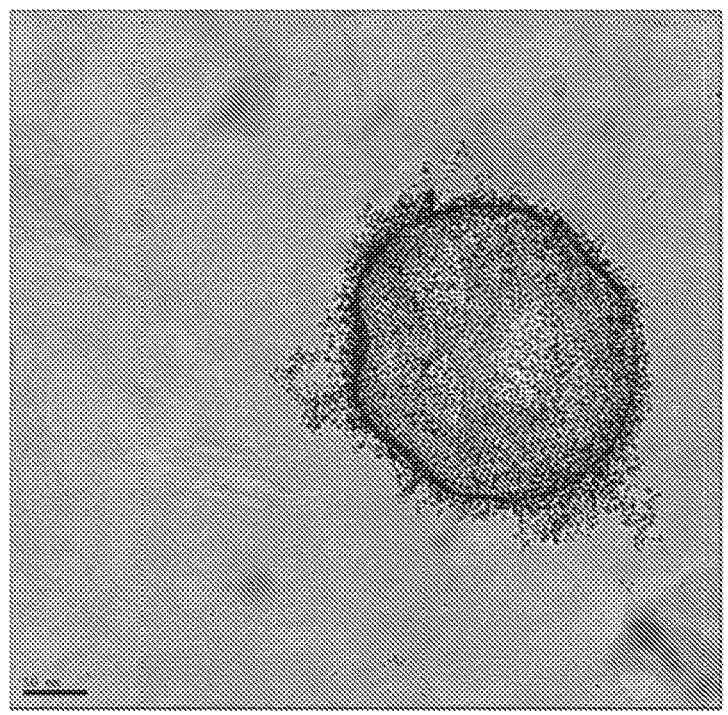

FIGS. 3a and 3b are optical micrographs showing the emulsion droplets comprising a Pt-PVP emulsifier and a hexadecane core. FIG. 4 is a cryoTEM image of the emulsion droplets.

Example 3: Formation of a Gold Film by Electroless Plating

The following procedure was used to form a continuous gold film on the surface of the emulsion droplets of Example 2 by electroless plating.

0.5 ml of the emulsion droplets of Example 2 was added to a plating solution consisting of 5 ml of a 0.2 wt % solution of PVP (PVP, 40 kDa, Fluka), 10 ml of Milli-Q water, 1 ml of a 40 mM solution of $HAuCl_4$ (99.999%, Aldrich) and 1 ml of a 60 mM solution of hydrogen peroxide (35 wt % in $H_2O$). The mixture was agitated on a carousel for 5 minutes to form a gold film around the emulsion droplets. The capsules were washed by removing the supernatant and replacing with Milli-Q water.

Figure 5:
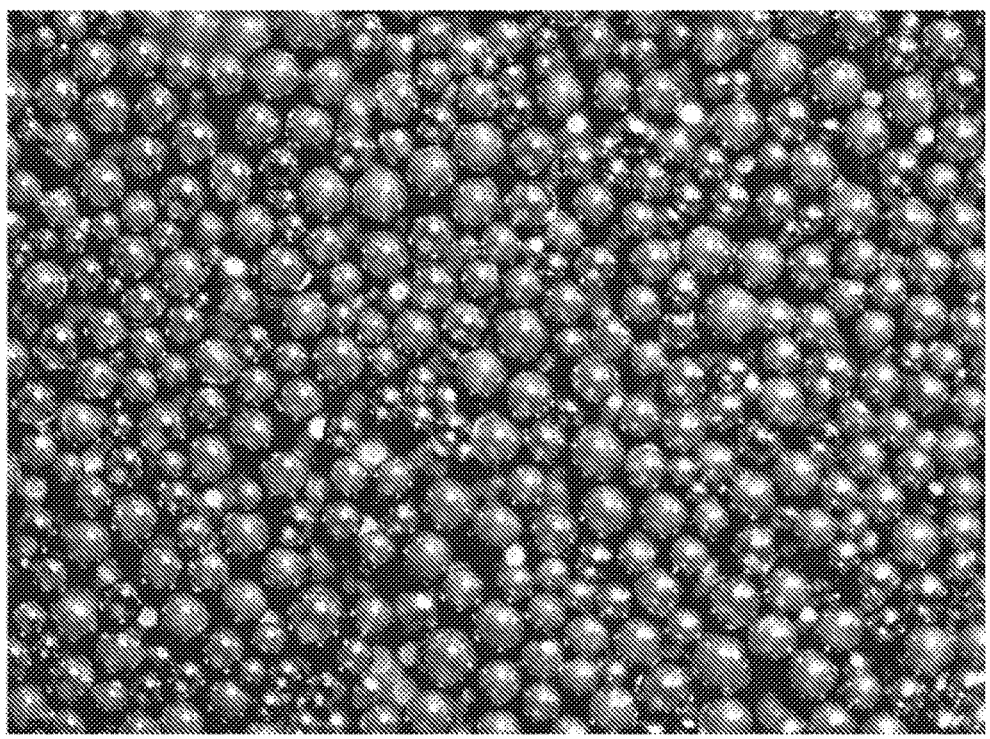
Figure 6A:
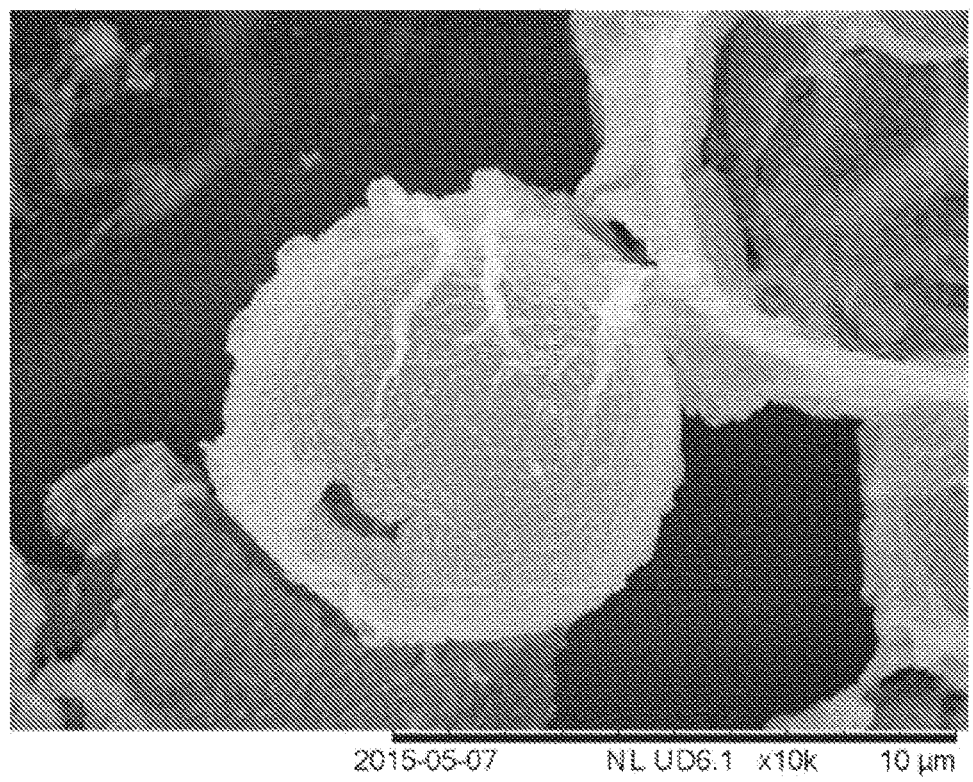
FIGS. 6a and 6b are SEM images showing the continuous gold film.
Figure 6B:
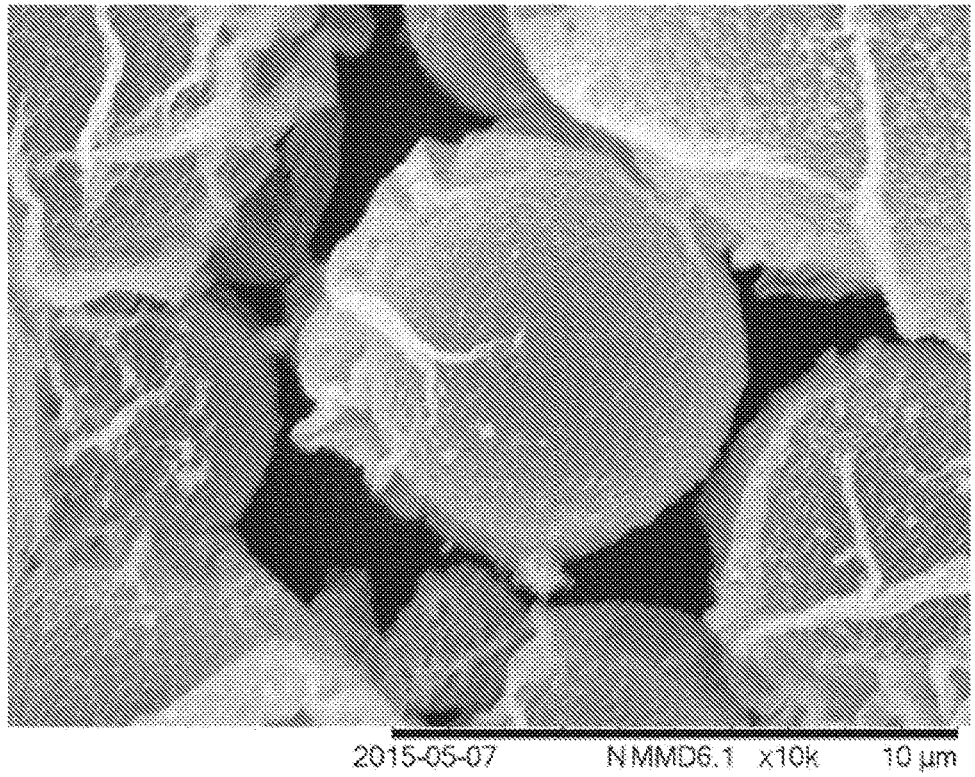

FIG. 5 is a reflected light optical micrograph showing the microcapsules having a continuous gold film on their surface. FIGS. 6a and 6b are SEM images showing the continuous gold film.

Example 4: Preparation of Charge-Stabilized Gold Nanoparticles

The following procedure was used to prepare borohydride-stabilized gold nanoparticles.

A 50 mM solution of $AuCl_4^-$ was prepared by dissolving 0.1669 g $HAuCl_4$ (99.999%, Aldrich) with 0.049 g of hydrogen chloride (37%, Merck), i.e. an equivalent molar concentration, in 10 ml of Milli-Q water. A 50 mM solution of $NaBH_4$ was prepared by dissolving 0.189 g of $NaBH_4$ (≥98.0%, Aldrich) with 0.2 g of NaOH, i.e. an equivalent molar concentration, in 100 ml of Milli-Q water. 1 ml of the $AuCl_4^-$ solution was added dropwise to 96 mL of Milli-Q water. 3 ml of the $NaBH_4$ solution was then added rapidly, and the solution stirred for 1 minute to release hydrogen gas molecules. A color change from pale yellow to red was observed on addition of the $NaBH_4$ solution, which is characteristic of the precipitation of gold nanoparticles.

Example 5: Preparation of Emulsion Droplets Comprising a Diblock Copolymer Emulsifier Disposed Around a Hexadecane Core The following procedure was used to prepare emulsion droplets comprising a diblock copolymer emulsifier disposed around a hexadecane core. The emulsion droplets were prepared by oil-in-water emulsification.

A poly(butylacrylate)-b-(trimethylaminoethyl methacrylate) diblock copolymer was synthesized via a Reversible Addition-Fragmentation Transfer (RAFT) polymerization route (see e.g. Zhao et al., Polymer Chemistry, 2013, 4(6), 2140-2150; and Tang et al., Macromolecular Chemistry and Physics, 2006, 207(19), 1718-1726).

4 ml of hexadecane (99%, Aldrich) was added to 16 ml of a 0.2 wt % solution of the diblock copolymer. The mixture was emulsified using a homogenizer (IKA T25 Ultra-Turrax) at 24000 rpm for 2 min. The resulting emulsion was agitated on a carousel for 30 minutes. Once a fully creamed emulsion was obtained, the emulsion was washed with Milli-Q water.

Example 6: Adsorption of Charge-Stabilized Gold Nanoparticles onto Emulsion Droplets The following procedure was used to adsorb the charge-stabilized gold nanoparticles of Example 4 onto the surface of the emulsion droplets of Example 5.

The emulsion of Example 5 was added to the gold nanoparticles of Example 4 and Milli-Q water, and then agitated. Once a fully creamed emulsion was obtained, the emulsion was washed.

Example 7: Formation of Silver Film by Electroless Plating

The following procedure was used to form a continuous silver film on the emulsion droplets of Example 6 by electroless plating.

Whilst stirring at 800 rpm, 0.5 ml of 0.1 M $AgNO_3$ (Fischer) was added dropwise to 17.5 mL of water, followed by the dropwise addition of 2 ml of the emulsion droplets of Example 6. Then 50 μl of formaldehyde and 25 μl of ammonia (25% in $H_2O$, Sigma) was added to the mixture. The dispersion was then stirred for 10 min to form the microcapsules.

Example 8: Performance of Microcapsules Under the Ethanol Stability Test

Microcapsules comprising a hexadecane core, a Pt-PVP emulsifier and a continuous gold film were prepared following the procedures described in Examples 1, 2 and 3. The microcapsules were then tested for their ability to retain the liquid core material using the Ethanol Stability Test described herein.

Figure 7:
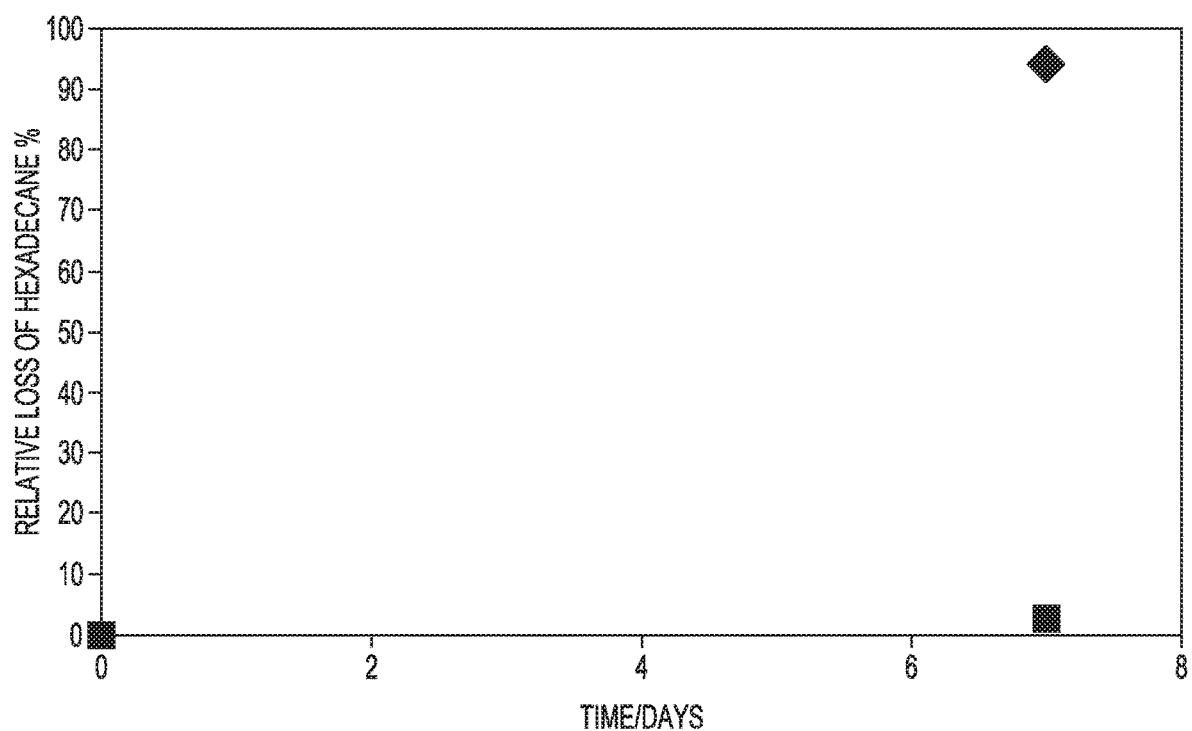
FIG. 7 is a graph showing the performance of microcapsules comprising a hexadecane core, a Pt-PVP emulsifier and a continuous gold film (see the data points indicated as squares) under the Ethanol Stability Test described herein. Also provided is a data point obtained after fracturing the microcapsules at the end of the experiment (see the data point indicated as a diamond).

FIG. 7 is a graph showing the performance of the microcapsules under the Ethanol Stability Test (see the data points indicated as squares). Also shown in FIG. 7 is a data point obtained following fracture of the microcapsules at the end of the experiment (see the data point indicated as a diamond), confirming that the liquid core material had been encapsulated. It can be seen from these data that the microcapsules exhibited negligible leakage of the liquid core material.

Microcapsules comprising a hexadecane core, a diblock copolymer emulsifier having borohydride-stabilised gold particles adsorbed thereon and a continuous silver film were prepared following the procedures described in the above Examples. The microcapsules were then tested for their ability to retain the liquid core material using the Ethanol Stability Test described herein.

The microcapsules exhibited negligible leakage of the liquid core material.

Example 9: Hair Coloring/Bleaching Composition

| Ingredient | Weight Percent |
| --- | --- |
| Water | 70.965% |
| Disodium EDTA | 0.045% |
| Aculyn 22 | 0.75% |
| Aculyn 33 | 2.5% |
| Simethicone | 0.025% |
| Microcapsules (core material includes $H_2O_2$ 35 wt % of the microcapsule | 12.855% |
| Decyl glucoside | 1% |
| Disodium phosphate | 0.04% |
| Sodium lauryl sulphate | 0.05% |
| Phosphoric acid | 0.08% |
| Propylene glycol | 0.05% |
| Erythorbic acid | 0.2% |
| Sodium sulphate | 0.8% |
| Ammonium hydroxide (25% solution) | 4.35% |
| Crodafos CES ® | 2.5% |
| Cetearyl alcohol | 0.375% |
| Steareth-200 | 0.125% |
| Xanthan gum | 0.04% |
| Propylene glycol | 0.25% |
| Sodium hydroxide | 0.11525% |

All percentages, parts and ratios recited herein are calculated by weight unless otherwise indicated. All percentages, parts and ratios are calculated based on the total composition unless otherwise indicated. Unless otherwise noted, all component or composition levels are in reference to the active portion of that component or composition, and are exclusive of impurities, for example residual solvents or by-products which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A microcapsule comprising an emulsion droplet encapsulated by a metallic film, wherein the emulsion droplet comprises an emulsifier disposed around a liquid core material, wherein the emulsion droplet comprises particles of a first metal selected from palladium, platinum, silver, gold, copper, nickel, tin, and a combination thereof, a second metal selected from silver, gold, nickel, copper, and a combination thereof, the metallic film is formed on said emulsion droplet, and wherein the liquid core material comprises a volatile material, and the particles of the first metal are nanoparticles, the density of said particles of the first metal on the emulsion droplet is from 0.0001 g/m² to 0.01 g/m² of the surface area of the emulsion droplet the metallic film has:
  (i) a maximum thickness of 1000 nm; and
  (ii) a minimum thickness of 1 nm;

the emulsifier further comprises a stabilizer stabilizing the nanoparticles; and the nanoparticles of the first metal are charge-stabilized nanoparticles.

2. A microcapsule according to claim 1, wherein the emulsifier is cross-linked.

3. A microcapsule according to claim 1, wherein the microcapsule has a particle size from 0.1 micron to 500 microns.

4. A microcapsule according to claim 1, further comprising an polymer film at least partially over coating.

5. A process for preparing a microcapsule, the process comprising the steps:
  providing an emulsion droplet comprising an emulsifier disposed around a liquid core material; and
  forming a metallic film on the emulsion droplet such that the emulsion droplet is encapsulated by the metallic film;
  wherein the emulsion droplet comprises particles of a first metal selected from palladium, platinum, silver, gold, copper, nickel, tin, and a combination thereof and the step of forming the metallic film comprises forming a layer of a second metal selected from silver, gold, nickel, copper, and a combination thereof on said particles of the first metal, and wherein the liquid core material comprises a volatile material, and the particles of the first metal are nanoparticles, the density of said particles of the first metal on the emulsion droplet is from 0.0001 g/m² to 0.01 g/m² of the surface area of the emulsion droplet the metallic film has:
  (i) a maximum thickness of 1000 nm; and
  (ii) a minimum thickness of 1 nm;

the emulsifier further comprises a stabilizer stabilizing the nanoparticles; and the nanoparticles of the first metal are charge-stabilized nanoparticles.

6. A consumer product comprising a composition, said composition comprising:
  an adjunct material; and
  a plurality of microcapsules according to claim 1.

7. A consumer product according to claim 6, wherein the liquid core material is selected from the group consisting of perfumes; brighteners; insect repellants; silicones; waxes; flavors; vitamins; fabric softening agents; depilatories; skin care agents; enzymes; probiotics; dye polymer conjugate; dye clay conjugate; perfume delivery system; sensates; anti-bacterial agents; dyes; pigments; bleaches; flavorants; sweeteners; waxes; pharmaceuticals; fertilizers; herbicides and mixtures thereof.

8. A consumer product according to claim 6, wherein said adjunct ingredient comprises from 0.01% to 99.9% ethanol, by weight of the composition.

9. A microcapsule according to claim 1, wherein the first metal is selected from palladium, platinum, silver, gold, copper, nickel, tin, and a combination thereof.

* * * * *